United States Patent [19]

Pioch

[11] Patent Number: 4,474,794

[45] Date of Patent: Oct. 2, 1984

[54] N-THIAZOLYLMETHYLTHIOALKYL-N[1]-ALKENYL (OR ALKYNYL)GUANIDINES AND RELATED COMPOUNDS

[75] Inventor: Richard P. Pioch, Indianapolis, Ind.

[73] Assignee: Eli Lilly and Company, Indianapolis, Ind.

[21] Appl. No.: 360,034

[22] Filed: Mar. 19, 1982

[51] Int. Cl.[3] .................. C07D 277/30; A61K 31/425
[52] U.S. Cl. ..................................... 424/270; 544/133; 546/209; 548/202; 548/205
[58] Field of Search ................. 548/205, 202; 424/270

[56] References Cited

U.S. PATENT DOCUMENTS 4,200,578  4/1980  Algieri ................................. 548/193

Primary Examiner—Robert Gerstl
Attorney, Agent, or Firm—James L. Row; Arthur R. Whale

[57] ABSTRACT

N-alkenyl (or N-alkynyl)-N'-[2-(aminoalkyl)-4-thiazolylmethylthio]alkylguanidines, thioureas, ethenediamines and related compounds, $H_2$ receptor antagonists, useful in inhibiting gastric acid secretion in mammals.

3 Claims, No Drawings

N-THIAZOLYLMETHYLTHIOALKYL-N¹-ALKENYL (OR ALKYNYL)GUANIDINES AND RELATED COMPOUNDS

BACKGROUND OF THE INVENTION

Over the past few years, several research groups in, chiefly, England or the United States of America, have synthesized histamine $H_1$ or $H_2$-receptor antagonists. The $H_2$-receptor antagonists are useful in treating peptic ulcers. Broadly speaking, these compounds are substituted guanidines,

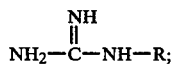

mercaptoamidines or isothioureas,

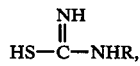

tautomeric with the thioureas

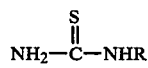

and ethanediamines,

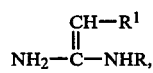

tautomeric with

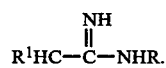

In these new $H_2$-receptor antagonists, the amidine or guanidine moiety usually occurs at one end of a bridging group; i.e., —$CH_2$—Y—$(CH_2)_2$— where Y is S, O, NH or $CH_2$. The other end of the bridging group has usually been an aromatic heterocycle, most frequently imidazole. The heterocyclic ring can be substituted.

The first drug recognized as a powerful $H_2$-receptor antagonist was a thiourea, burimamide—N-methyl-N'-(4-[4(5)-imidazolyl)]butyl)thiourea—having the following formula:

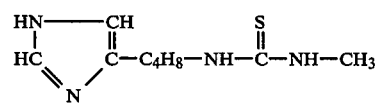

The pharmacological properties of this compound are disclosed in *The Pharmacological Basis of Therapeutics*, Goodman & Gilman 5th Ed. (MacMillan Publishing Co., Inc., New York) page 612. Burimamide was developed by a group of research workers headed by Black and Durant.

A second generation of histamine $H_2$-receptor antagonists comprised compounds developed by Black, Durant and co-workers with a structure more or less similar to that of burimamide, but in which there was a permissible interrupting group—oxygen, sulfur or NH—in the alkyl side chain attached to the hetero ring. The most prominent of this group of compounds has been cimetidine, chemically N-cyano-N'-methyl-N''-[2-([(5-methyl-1H-imidazol-4-yl)methyl]thio)ethyl]-guanidine, represented by the formula II below:

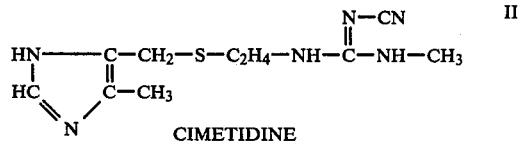

A large number of patents covering guanidines, thioureas, ethenediamines, etc., based upon several original filings (Ser. Nos. 230,451; 284,992; 385,027; 481,716; 816,420; 436,285; 542,971; 468,617; 384,993; and 385,027) have issued to Durant et al including, but not limited to, the following U.S. Pat. Nos. 3,950,333; 4,049,672; 4,022,797; 4,137,237; 4,024,271; 4,070,475; 4,154,844; 3,905,984; 4,027,026; 3,932,427; 4,018,928; 3,950,353; 4,053,473; 4,018,931; 4,069,372; 4,151,288; 4,000,296; 4,083,988; 4,129,657; 4,098,898; 4,166,856; 4,072,748; 3,971,786; 4,060,620; 3,876,647; 3,920,822; 3,897,444; 3,975,530; 4,226,874; 4,228,291; 4,230,865 and 4,221,802.

Other disclosed hetero ring systems in addition to imidazole include pyrazole, pyridine, pyrimidine, pyridazine, thiazole, isothiazole, oxazole, isoxazole, triazole, thiadiazole, benzimidazole and tetrahydroimidazo[1,5-a]pyridine, but the greatest emphasis has been on compounds having an imidazole ring system.

Patents referring to thiazole or oxazole ring systems are of particular relevance to this invention. The two basic disclosures of such compounds by the Durant group are contained in U.S. Pat. No. 3,950,333 and U.S. Pat. No. 3,950,353, both of which are continuations-in-part of Ser. No. 290,584 which was in turn a continuation-in-part of Ser. No. 230,451. In U.S. Pat. No. 3,950,333, the disclosure relating to thiazoles begins at Example 115, column 37. Thiazoles substituted with a chloro or an alkyl group are described. The thiazole nucleus is then attached at the 2- or 4-position of the thiazole ring to an alkylthioalkyl side chain terminating in an N-cyano-N'-methylguanidine. This disclosure is followed by similar disclosures for isothiazoles, oxazoles and isoxazoles. The disclosure in U.S. Pat. No. 3,950,353 relating to thiazoles begins at Example 110, column 37. Here, substantially the same thiazole nucleus is attached via a bridging group to an N-methylthiourea. A similar disclosure is present for isothiazoles, oxazoles and isoxazoles. U.S. Pat. No. 4,022,797, a division, specifically claims cyanoguanidine derivatives and U.S. Pat. No. 4,137,234, another divisional patent, specifically claims thioureas.

U.S. Pat. No. 4,000,296 to the Durant group discloses and claims a group of N-alkyl or N-arylsulfonyl-N'-alkyl-N''(heterocyclealkylthioalkyl)guanidines in which the heterocycle can be thiazole, isothiazole, oxazole or isoxazole. Alkyl, alkylaminoalkyl and alkyloxyalkyl bridging groups (connecting the heterocycle to the substituted guanidine group) are also disclosed. Substituted heterocycles belonging to any of the above classes of $H_2$ receptor antagonists are not disclosed. U.S. Pat. No. 4,166,856, also originating with the Durant group, discloses and claims a number of imidazoles and thiazoles carrying the usual alkylthioalkyl-guanidine, -thiourea or -ethenediamine side chain, which side chain is invariably attached at the 2-position of the heterocyclic ring.

Another group of investigators under Yellin has disclosed—see U.S. Pat. Nos. 4,165,377, 4,234,735 and 4,165,378—certain novel thiazoles having a side chain such as those discussed above attached at the 4-position of the thiazole ring; i.e., an alkylthioalkyl-guanidine, -ethenediamine or -thiourea group but also bearing a guanidino group in the 2-position of the thiazole. Alkylene, alkenylene and alkyloxyalkyl bridging groups are disclosed. A representative compound is 2-guanidino-4-[2-(2-cyano-3-methylguanidino)-ethylthiomethyl]-thiazole which is said to have greatly increased activity over cimetidine.

A third research group at Allen and Hanburys Ltd. has prepared compounds with a furan ring carrying the standard alkylthioalkyl (or alkyloxyalkyl or alkyl) side chain terminating in a substituted guanidine or ethenediamine group, and also having a dialkylaminoalkyl substituent attached at a second position in the furan ring—see U.S. Pat. Nos. 4,128,658 and 4,168,855. Belgian Pat. Nos. 867,105 and 867,106 disclose the corresponding aminoalkyl thiophenes and benzenes. Several of the compounds thus produced have a greater H$_2$ receptor antagonist activity than cimetidine, the most prominent of which is ranitidine

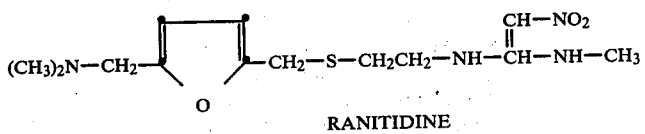

RANITIDINE

U.S. Pat. No. 4,233,302 from Glaxo also discloses dialkylaminoalkyl-substituted thiophenes and furans as H$_2$-receptor antagonists.

Finally, a research group at Bristol-Myers have issued several U.S. patents involving different heterocycles. The first of these, U.S. Pat. No. 4,203,909, relates to furans carrying an alkylthioalkyl-guanidine (or thiourea or ethenediamine) side chain terminating in an alkynylamino group in the 2-position, and an aminoalkyl side chain in the 5-position. One of their compounds, 1-nitro-2-(2-propynylamino)-2-(2-[(5-dimethylaminomethyl-2-furyl)methylthio]ethylamino)ethylene, is said to have 7.45 times the activity of cimetidine in a standard H$_2$-receptor assay. A second patent, U.S. Pat. No. 4,200,578, covers broadly thiazoles substituted with an alkylthioalkylguanidine (or thiourea or ethenediamine) side chain, and again carrying an obligatory alkynyl group in the terminal portion. Other permissible substituents in the thiazole ring include alkyl, guanidino or aminoalkyl. Despite the broad disclosure, the actual working examples (compounds actually prepared) in U.S. Pat. No. 4,200,578 are limited to thiazoles carrying the alkylthioalkylguanidine, etc. side chain in the 2-position of the thiazole ring except for a few compounds in which the side chain is carried in the 4-position, but in which there is an obligatory guanidino group in the 2-position. Synthetic Schemes I through VIII of the patent are suitable only for preparing 2-substituted thiazoles. Example 17 discloses thiazoles with a dimethylaminomethyl group substituted in the 4-position and the methylthioethyl side chain in the 2-position. The side chain terminates in a N-alkynyl 2-nitro-1,1-ethenediamine group. The compound, 1-nitro-2-(2-propynylamino)-2-(2-[(4-dimethylaminomethylthiazol-2-yl)methylthio]ethylamino)ethylene, also named as N-(2-propynyl)-N-2-(2-dimethylaminomethyl-4-thiazolylmethylthio)ethyl 2-nitro-1,1-ethenediamine, is specifically disclosed.

U.S. Pat. No. 4,200,760 has a similar disclosure of an ethenediamine carrying a alkynylamine group attached by a bridging group to an imidazole ring. Pyridine is the heterocycle in U.S. Pat. No. 4,250,316. However, a recent Bristol-Myers Belgian Pat. No. 885,089, published Mar. 4, 1981, same as U.K. Pat. No. 2,067,987, discloses a group of H$_2$-receptor antagonists among which are included compounds of the formula

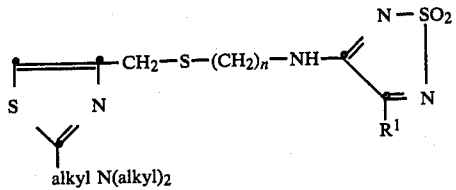

alkyl N(alkyl)$_2$

One compound specifically disclosed is prepared from 2-(2-dimethylaminomethyl-4-thiazolylmethylthio)ethylamine—See Example 22, part E page 72 et seq.

Many of the above cited patents disclose alkenyl groups as permissible substituents on one guanidine nitrogen; ie., U.S. Pat. No. 4,098,898 and 4,166,856 disclose the allyl group.

To summarize, thiazoles in which there is a 4-alkylthioalkylguanidine (or thiourea or ethenediamine) side chain are known wherein the thiazole group can be substituted in the 2- or 5-position with guanidino, methyl, chloro and aminoalkyl. Generic disclosures of thiazoles substituted with an aminoalkyl group at one position in the thiazole ring are in the art. These thiazoles have, at a second position in the thiazole ring, a bridging alkylthioalkyl, alkylene, alkenylene or alkyloxyalkyl group terminating in a substituted guanidine group, which carries an N-alkynyl or N-alkenyl group. N-(2-Propynyl)-N'-2-(4-dimethylaminomethyl-2-thiazolylmethylthio)ethyl-2-nitro-1,1-ethenediamine is specifically disclosed in Algieri et al, U.S. Pat. No. 4,200,574, Example 17.

SUMMARY OF THE INVENTION

This invention provides compounds of the formula

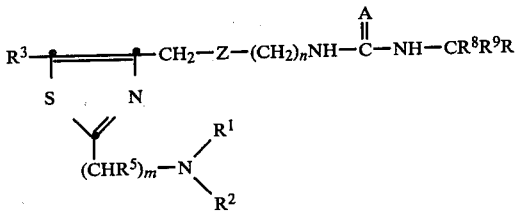

wherein each of R$^1$ and R$^2$ are individually H or (C$_1$-C$_4$) alkyl, one of R$^1$ and R$^2$ can be benzyl or benzoyl, and when taken together with the nitrogen to which they are attached, form a heterocyclic ring containing from 5 to 7 atoms and 1 to 2 heteroatoms; except that only one of $R^1$ and $R^2$ can be H when Z is $CH_2$;

$R^3$ is H or $(C_1-C_3)$alkyl;

Z is O, S or $CH_2$;

n is 2 or 3 when Z is O or S and n is 1, 2 or 3 when Z is $CH_2$;

$R^5$ is H or $CH_3$;

m is 1, 2 or 3;

wherein A is N—CN, N—$NO_2$, N—$(C_1-C_4)$alkyl, CH—$NO_2$, S, O, NH, N—$SO_2$-aryl, N—$SO_2$—$(C_1-C_4)$alkyl, N—CO—$NH_2$, N—CO—$(C_1-C_4)$alkyl; N—$CO_2$—$(C_1-C_4)$alkyl; CH—$SO_2$-aryl or CH—$SO_2$—$(C_1-C_4)$alkyl; wherein aryl is phenyl, halophenyl, $(C_1-C_4)$alkylphenyl or $(C_14-C_4)$-alkyloxyphenyl; $R^8$ and $R^9$ are individually H, $CH_3$ or $C_2H_5$ such that the total number of carbon atoms in the group $CR^8R^9R$ is less than 7; R is $(C_2-C_4)$ alkenyl or $(C_2-C_4)$ alkynyl; and pharmaceutically acceptable acid addition salts thereof.

Bases falling within the scope of the above formula include:

N-allyl-N'-2-(2-dimethylaminoethyl-5-methyl-4-thiazolylmethylthio)ethylguanidine N-methallyl-N'-3-[2-(methylethylaminomethyl)-4-thiazolylmethylthio]propylguanidine.

N-crotyl-N'-2-(2-aminomethyl-5-n-propyl-4-thiazolylmethylthio)ethyl-N''-nitroguanidine N-methallyl-N'-2-[2-(diethylaminoethyl)-4-thiazolylmethylthio]ethyl-N''-p-chlorophenylsulfonylguanidine N-2-pentynyl-N'-2-(2-methylaminomethyl-5-methyl-4-thiazolylmethylthio)ethylthiourea N-2-pentenyl-N'-3-(2-[2-(ethylaminoethyl)]-5-ethyl-4-thiazolylmethylthio)propylguanidine N-2-ethylpropenyl-N'-2-(2-[2-(diethylamino)-propyl]-5-methyl-4-thiazolylmethylthio)ethyl 2-(o-bromophenylsulfonyl)-1,1-ethenediamine or 1-(o-bromophenylsulfonyl)-2-(2-ethylpropenylamino)-2-(2-[2-(diethylaminopropyl)-5-ethyl-4-thiazolylmethylthio]ethylamino)ethylene N-2-methyl-2-butenyl-N'-2-(2-isopropylaminomethyl-4-thiazolylmethylthio)ethyl 2-methane sulfonyl-1,1-ethenediamine N-2-pentenyl-N'-3-[2-[2-(diethylamino)ethyl]-5-propyl-4-thiazolylmethylthio]propyl 2-nitro-1,1-ethenediamine.

N-(1-methyl-2-butenyl)-N'-2-(2-n-propylaminomethyl-5-ethyl-4-thiazolylmethylthio)ethyl 2-o-tolylsulfonyl-1,1-ethenediamine N-(1,1-dimethylpropargyl)-N'-2-[2-(ethyl-n-propyl)aminomethyl-5-n-propyl-4-thiazolylmethylthio]ethyl 2-nitro-1,1-ethenediamine.

N-2-butynyl-N'-2-(2-piperidinomethyl-4-thiazolylmethylthio)ethyl-N''-cyanoguanidine N-allyl-N'-3-(2-aminomethyl-4-thiazolylmethylthio)propyl 2-nitro-1,1-ethenediamine N-crotyl-N'-4-(2-ethylaminomethyl-5-methyl-4-thiazolyl)-1-butyl-N''-cyanoguanidine N-2-(3-Butyn-2-yl)-N'-2-(2-dimethylaminomethyl-4-thiazolylmethylthio)ethyl 2-nitro-1,1-ethenediamine N-2-pentenyl-N'-2-[2-(4-morpholinomethyl-5-ethyl-4-thiazolylmethyloxy]ethylguanidine N-2-pentynyl-N'-3-(2-(1-pyrrolidinomethyl)-4-thiazolylmethyloxy)propylurea.

N-methallyl-N'-3-[2-(methylaminopropyl)-4-thiazolylmethyloxy]propylthiourea

N-2-butynyl-N'-3-[2-(ethylaminoethyl)-4-thiazolyl]-propylguanidine.

N-methallyl-N'-3-[2-diethylaminomethyl-5-methyl-4-thiazolylmethylthio]propyl-N''-nitroguanidine.

N-dimethylpropargyl-N'-2-[2-(di-n-propyl)-aminomethyl-4-thiazolylmethylthio]ethyl-N''-methoxy-carbonylguanidine N-2-methyl-2-butenyl-N'-5-(2-[2-(diethyl)-aminoethyl]-4-thiazolyl)pentyl-N''-acetylguanidine N-allyl-N'-4-[2-(1-pyrrolidino)methyl)-4-thiazolyl]butyl-N''-aminocarbonylguanidine.

N-methallyl-N'-2-[2-(4-morpholinomethyl)-5-methyl-4-thiazolylmethylthio]ethyl 2-nitro-1,1-ethenediamine N-2-ethylallyl-N'-2-[2-(1-pyrrolidinomethyl)-4-thiazolylmethylthio]ethyl 2-methanesulfonyl-1,1-ethenediamine and the like.

Preferred compounds are those wherein $R^1$ and $R^2$ individually represent hydrogen or $(C_1-C_4)$alkyl, benzyl or benzoyl; in which one only of $R^1$ and $R^2$ may represent benzyl or benzoyl and the other is $(C_1-C_4)$-alkyl; or wherein $R^1$ and $R^2$ taken together with the adjacent nitrogen atom represent a piperidino, pyrrolidino or morpholino group, provided that only one of $R^1$ and $R^2$ can be hydrogen when Z is $CH_2$; wherein $R^3$ is hydrogen or $(C_1-C_4)$alkyl; $R^5$ is hydrogen or methyl; A is N—CN, N—$NO_2$, N—$(C_1-C_4)$alkyl, CH—$NO_2$, S, O, NH, N—$SO_2$-aryl, N—$SO_2$—$(C_1-C_4)$alkyl, N—CO—$NH_2$, N—CO—$(C_1-C_4)$alkyl, N—$CO_2$—$(C_1-C_4)$alkyl, CH—$SO_2$-aryl or CH—$SO_2$—$CH_3$, wherein aryl is phenyl, halophenyl, $(C_1-C_4)$-alkylphenyl or $(C_1-C_4)$alkyloxyphenyl; and R is vinyl or ethinyl and the pharmaceutically-acceptable, non-toxic acid-addition salts thereof.

Further preferred features possessed by the $H_2$-receptor antagonists of the invention are those listed below:

(a) Z is S;
(b) n is 2;
(c) $R^3$ is hydrogen;
(d) $R^5$ is hydrogen;
(e) m is 1;
(f) $R^1$ and $R^2$ are methyl;
(g) the

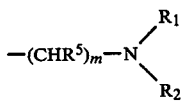

group is dimethyl aminomethyl;
(h) A is NCN or $CHNO_2$;
(i) R is ethynyl, and $R^8$ and $R^9$ are H.

In Formula XX, the term $(C_1-C_4)$ alkyl includes methyl, ethyl, n-propyl, isopropyl, n-butyl, isobutyl etc. Thus, the term $(C_1-C_4)$alkylphenyl would include o, m and p-tolyl, o, m, and p-ethylphenyl and the like. Similarly, the term $(C_1-C_4)$alkyloxyphenyl includes o, m, p-anisyl, o, m, and p-ethoxyphenyl and the like. The term halophenyl includes o, m, and p-chlorophenyl, bromophenyl, fluorophenyl and iodophenyl.

The terms $(C_2-C_4)$alkenyl or $(C_2-C_4)$alkynyl include vinyl, allyl, propargyl, 2-ethylvinyl, 2-methylvinyl, 2,2-dimethylvinyl, ethinyl, 2-methylethinyl, 1-butynyl, and the like.

The pharmaceutically-acceptable acid addition salts of the compounds of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalane-1-sulfonate, naphthalane-2-sulfonate and the like salts.

Compounds according to XX above have at least one basic center, the aminoalkyl group at C-2 of the thiazole ring but may have a second salt-forming group. For example, the substituted amidine or guanidine terminal group which can also have nitrogens present which one of which may, depending on the substitution pattern, be sufficiently basic to form a salt with one of the stronger non-toxic acids. Thus, di salts of hydrochloric, hydrobromic and similar strong acids are preparable with many of the compounds represented by XX.

The compounds of this invention wherein Z is S or O—in other words, a heteroatom—are conveniently prepared from a 2-(2aminoalkyl-4-thiazolylmethylheteroatom)alkyl amine. The preparation of these starting materials is illustrated in Flow Chart A below using a compound in which the heteroatom is sulfur for exemplary purposes only.

FLOW CHART A

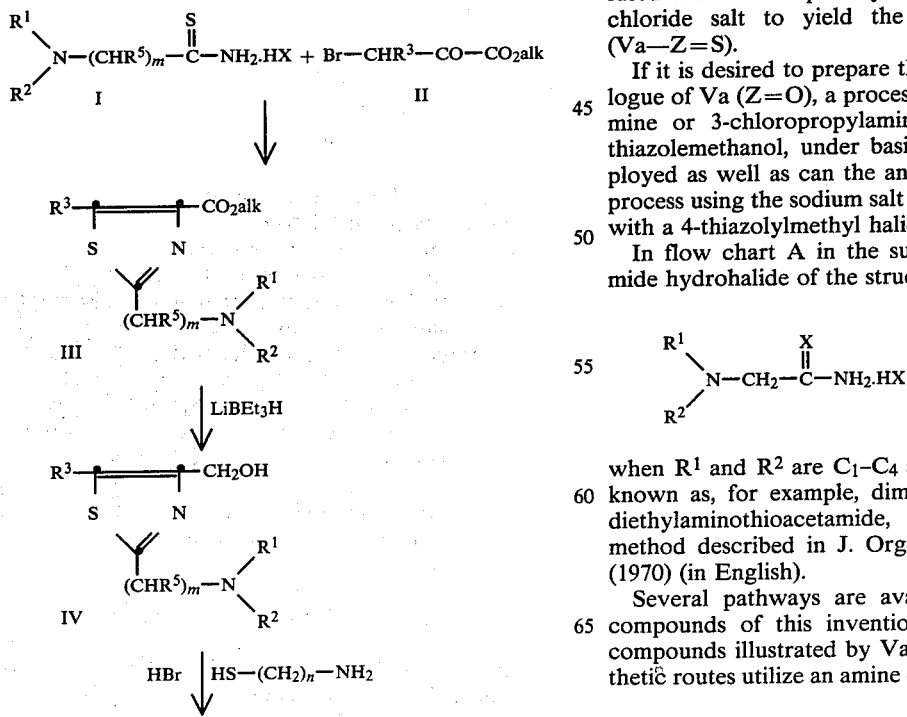

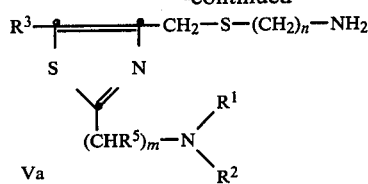

In the above Flow Chart, alk is conveniently methyl or ethyl and $R^1$, $R^2$, $R^3$, $R^5$, m and n have the same meaning as hereinabove.

In accordance with the above procedure, an acid addition salt of an aminoalkylthioacetamide (I) is reacted with a beta-bromo-alpha-ketoester (II) such as ethyl bromopyruvate ($R^3$=H) to yield an alkyl (methyl or ethyl) 2-(aminoalkyl)-4-thiazolecarboxylate (III). Reduction of this ester with a suitable hydride reducing agent such as lithium triethylborohydride, lithium aluminumhydride, sodium borohydride, diisobutylaluminumhydride and the like yields the corresponding hydroxymethyl compound (IV). Reaction of the 4-hydroxymethylthiazole with cysteamine or its higher homologue, 3-mercaptopropylamine, in the presence of acid yields directly a (2-aminoalkyl-4-thiazolylmethylthio)alkylamine (Va) optionally substituted with an alkyl group in the 5-position of the thiazole ring.

In the process indicated in Flow Chart A, in going from IV to Va, the hydroxymethyl group can be halogenated as with thionylchloride to yield a 4-chloromethylthiazole and the chlorinated compound in turn reacted with the sodium salt of the particular mercaptoalkylamine. In fact, any standard leaving group (a group labile to nucleophilic displacement) can be employed here in place of chloro in the chloromethyl side chain including for example p-tosyloxy, mesyloxy (methanesulfonyloxy), bromo, iodo and the like.

Alternatively, the 4-chloromethylthiazole hydrochloride (or other suitable acid addition salt) can be fused with a mercaptoalkylamine salt such as a hydrochloride salt to yield the desired primary amine (Va—Z=S).

If it is desired to prepare the side chain oxygen analogue of Va (Z=O), a process utilizing 2-chloroethylamine or 3-chloropropylamine to react with the 4-thiazolemethanol, under basic conditions, can be employed as well as can the analogous Williamson ether process using the sodium salt of the hydroxyalkylamine with a 4-thiazolylmethyl halide.

In flow chart A in the substituted aminothioacetamide hydrohalide of the structure

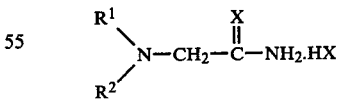

when $R^1$ and $R^2$ are $C_1$-$C_4$ alkyl, the compounds are known as, for example, dimethylaminothioacetamide, diethylaminothioacetamide, etc., preparable by the method described in J. Org. Chem., (Russia), 6, 884 (1970) (in English).

Several pathways are available for preparing the compounds of this invention from the intermediate compounds illustrated by Va. These pathways or synthetic routes utilize an amine of the generalized formula

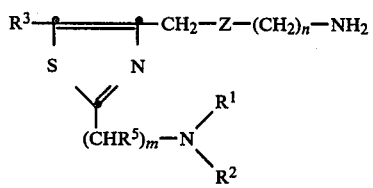

V wherein Z is S, O or CH$_2$, as a starting material. These routes are illustrated in Flow Charts B, C and D below. According to Flow Chart B, a starting primary amine, the ultimate product of Flow Chart A (Va), (Z=S) is reacted with, for example, an N-alkenyl (or N-alkynyl) 1-methylthio-2-nitroetheneamine. During the reaction, the elements of methylmercaptan are displaced and the final desired product (VIIa) is an N-2-(2-aminoalkyl-5-optionally-substituted-4-thiazolylmethylthio)alkyl-N'-alkenyl or alkynyl 2-nitro-1,1-diaminoethylene (or ethenediamine). Similarly, the primary amine (Va) can be reacted with an S-methyl-N-alkenyl (or N-alkynyl)-N'-cyanoisothiourea to form the desired product (VIa-)—an N-alkenyl (or N-alkynyl)-N'-2-(2-aminoalkyl-5-optionally substituted-4-thiazolylmethylthio)ethyl-N"-cyanoguanidine.

FLOW CHART B

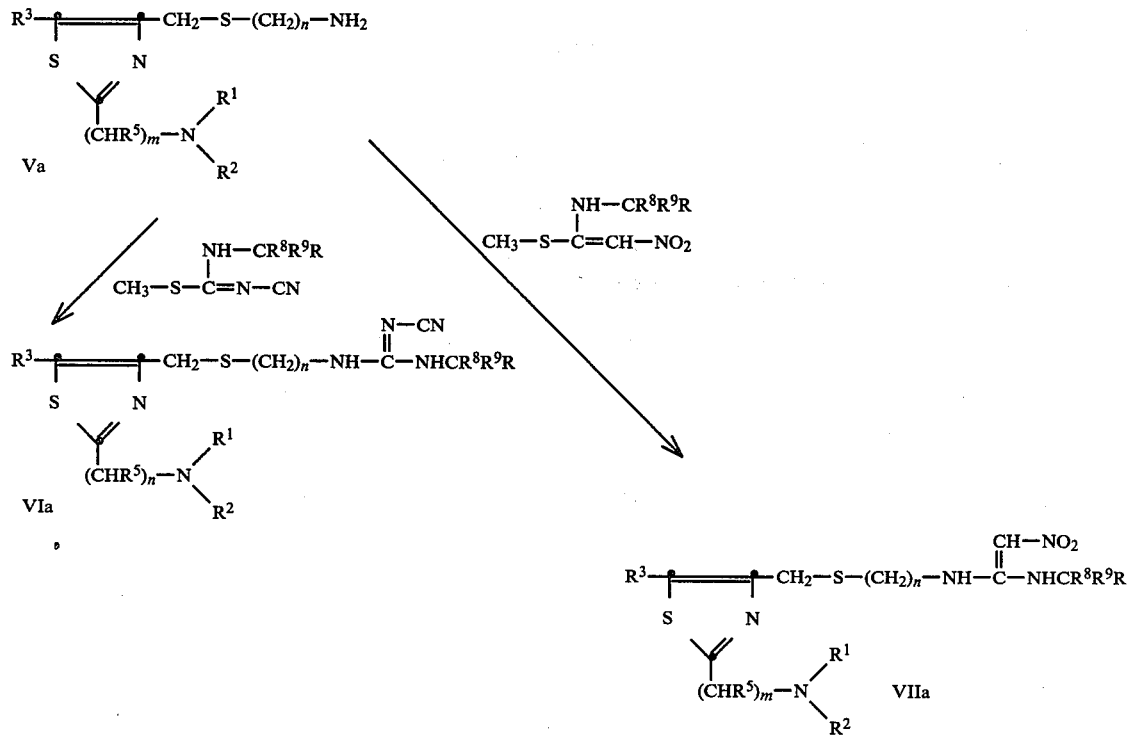

wherein R, R$^1$, R$^2$, R$^3$, R$^5$, R$^8$ and R$^9$, m and n have the same meaning as hereinabove, but R$^1$ and R$^2$ cannot both be H.

In the above reactions, it is apparent that in place of an N-alkenyl (or N-alkynyl)-1-methylthio-2-nitroethyleneamine, an N-alkenyl (or N-alkynyl) 1-methylthio-2-methylsulfonylethyleneamine (or 2-phenylsulfonylethyleneamine) could be used. If it is desired to prepare a compound of structure XX wherein A is N—SO$_2$-phenyl, the reagent used to prepare such N"-phenylsulfonylguanidines is dimethyl N-phenylsulfonylimidodithiocarbonate prepared by the general procedure of Ber., 99, 2885 (1966). The methylsulfonylguanidines are in turn produced from dialkyl N-methylsulfonylimidodithiocarbonates prepared in the same fashion. Similarly, it is apparent that an N-alkenyl or N-alkynyl 1-methylthio-2-arylsulfonylethyleneamine (or 2-methylsulfonylethyleneamine) could be used in place of the N-alkenyl (or N-alkynyl)-1-methylthio-2-nitroethyleneamine of the above flow chart. 2-Arylsulfonyl-1-methylthioethyleneamine, the intermediate containing a sulfonyl group, can be prepared by reacting, for example, a 2-arylsulfonyl-1,1-bis-methylthioethylene (prepared by the method of Bull., Soc. Chem. Fr., 637 (1973)) with one mole of an amine NH$_2$CR$^8$R$^9$R. The 2-methylsulfonyl derivatives useful as intermediates can be prepared in the same fashion.

Obviously, compounds corresponding to VI and VII in which O replaces S in the bridging group are prepared by substituting a 2-aminoalkyl-4-thiazolylmethyloxyalkylamine for Va in Flow Chart B.

Thus, in the general case, compounds of formula (XX) may be prepared by reacting the amine intermediate of formula V with a compound of the formula

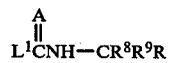

where L$^1$ is a leaving group, preferably for ease of preparation, a C$_1$–C$_5$ alkylthio, benzylthio or C$_2$–C$_4$ alkenylmethylthio group, A, R$^8$, R$^9$ and R being as previously defined.

The reactions of Flow Chart B should be effected in a polar solvent such as water, a C$_1$–C$_4$ alkanol or acetonitrile, preferably at a temperature of from 20° to 100° C., most preferably 40° to 50° C.

An alternate method of preparation of the compounds of this invention is illustrated in Flow Chart C. According to this procedure, the same requisite thiazole intermediate (V) is reacted with a 1,1-bis-methylthio-2-nitro (or arylsulfonyl or methylsulfonyl) ethylene to produce an N-2-[(2-aminoalkyl-5-optionally-substituted-4-thiazolyl)methylthio]ethyl 1-amino-1-methylthio-2-nitro (or arylsulfonyl or methylsulfonyl)ethyleneamine. Compounds wherein Z is O or $CH_2$ are prepared similarly.

are prepared similarly and react similarly to yield an analogous final product having an ethenediamine terminal group as in VII.

In going from V to IX, 1-methylsulfinyl-1-methylmercapto-2-nitroethylene can be used in place of 1,1-bis-methylmercapto-2-nitroethylene to yield the same intermediate IX since a methylsulfinyl group is displaced preferentially to a methylmercapto group.

Following the above procedure, in certain instances, a reactant such as VIII can be employed in which an $OCH_3$ group replaces the $SCH_3$. This methoxy group is replaceable by the amine $NH_2R^8R^9R$ as is the $S-CH_3$

FLOW CHART C

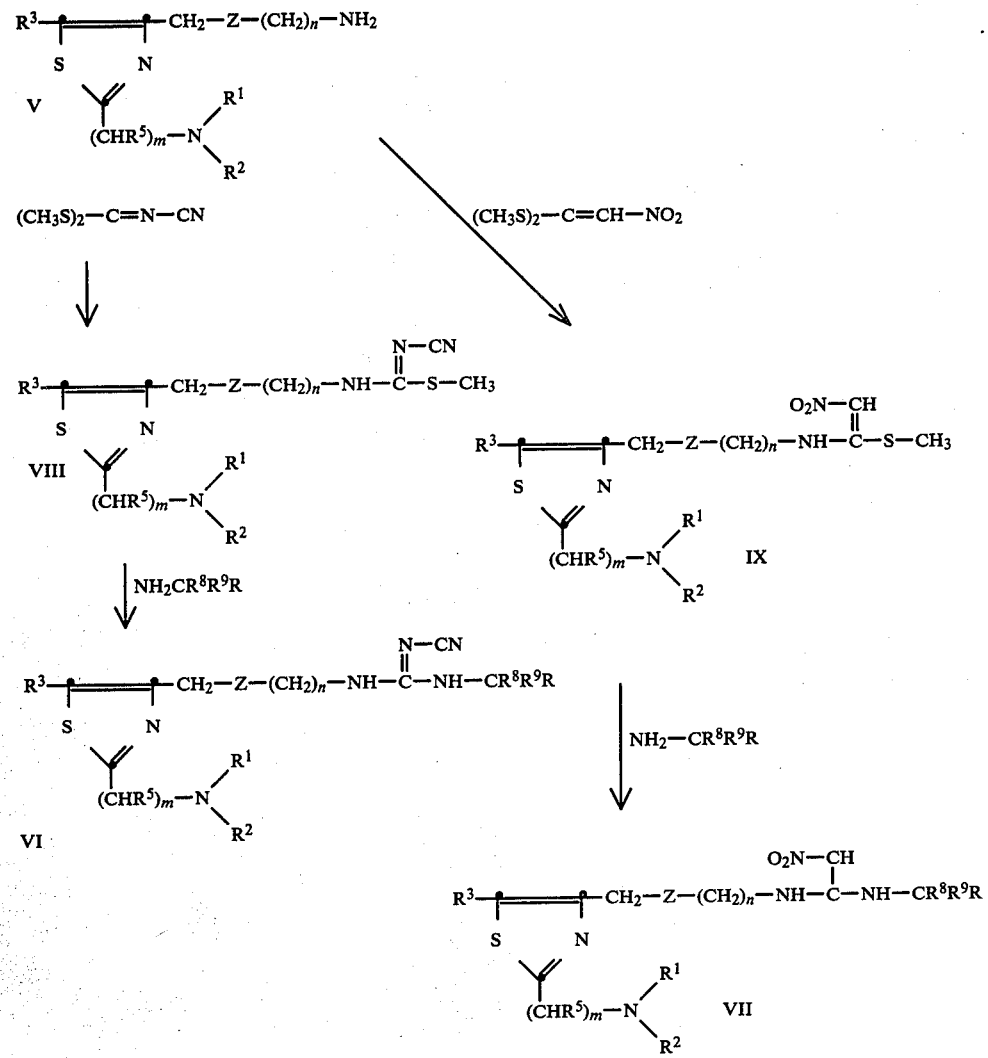

wherein Z, R, $R^1$, $R^2$, $R^3$, $R^5$, $R^8$ and $R^9$, m and n have the same meaning as hereinabove, except that both $R^1$ and $R^2$ cannot be H.

According to Flow Chart C, reaction of the methylmercapto compound VIII or IX with a primary amine $NH_2CR^8R^9R$ yields the desired product. For example, dimethylcyanodithioimidocarbonate will react with the thiazolylmethylthioalkylamine or other thiazolyl side chain amine (V) to produce an N-2-(2-aminoalkyl-5-optionally-substituted-4-thiazolylmethylthio)ethyl (or propyl)-S-methyl-N'-cyanopseudothiourea (VIII where Z is S). Reaction of this compound with the primary amine $NH_2CR^8R^9R$ again yields the desired product VI. Compounds in which A is $CH-NO_2$ etc. as in IX group illustrated above. For example, a compound of the formula $(CH_3O)_2-C=NCN$, or a compound with two different leaving groups such as

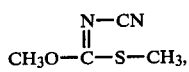

can be employed as a reactive intermediate.

Thus, in the general case, a compound of formula:

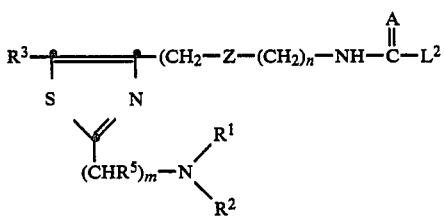

where L² is a leaving group, preferably a group of formula YR⁴, where R⁴ is lower alkyl and Y is S or O, can be reacted with an amine of formula NH₂CR⁸R⁹R to yield compounds of formula XX.

The reaction is preferably effected at a temperature from 20° to 100° C. in a polar solvent such as water or a $(C_1-C_4)$ alkanol.

A third type of formula XX compound coming within the scope of the above formula are the thioureas or ureas wherein A is Y. An example of the preparation of such compounds is illustrated in Flow Chart D.

FLOW CHART D

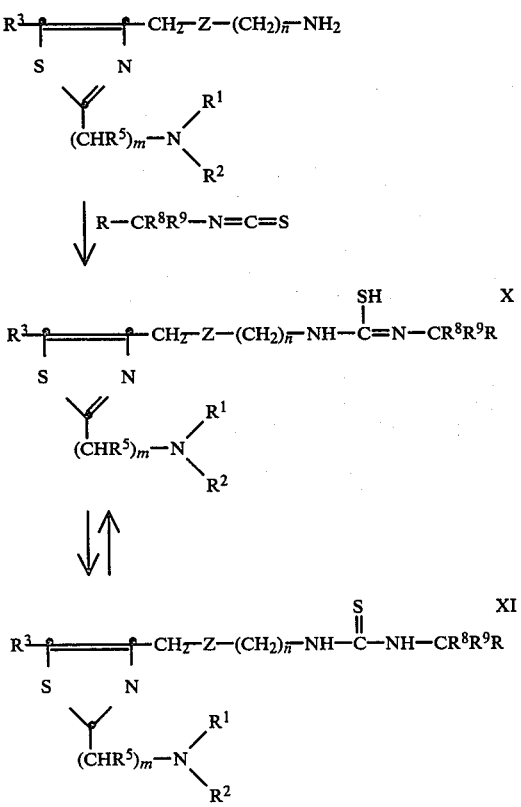

wherein R, R¹, R², R³, R⁵, R⁸, R⁹, Z, n and m have their previously assigned meanings, but only one of R¹ and R² can be H in a given molecule.

According to Flow Chart D, the starting amine, (V), for example a thiazolylmethylthioalkylamine (Z=S), is reacted with a suitably substituted isothiocyanate to yield directly the isothiourea (X) which compound is in equilibrium with the thiourea itself (XI). Similarly, an isocyanate, R—CR⁸R⁹—N=C=O, can be used to prepare the corresponding urea.

In the general case, compounds of formula XX may be prepared by reacting a compound of formula V with a reagent of the formula

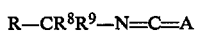

Where A is NCN, NSO₂aryl etc, the reagent is a carbodiimide; where A is CH—NO₂ etc, the reagent is a nitroketeneimine; where A is S, the reagent is an isothiocyanate etc.

The reaction is preferably effected in a polar solvent such as water, a $(C_1-C_4)$ alkanol or acetonitrile. When A is oxygen, the reaction should normally be effected in acetonitrile. Preferred reaction temperatures range from 20° to 100° C., most preferably from 40° to 50° C.

Compounds according to Formula XX above wherein A is N—CO—NH₂; i.e., having a terminal group of the structure

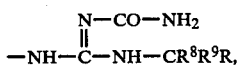

are prepared by hydration of the corresponding cyano compound,

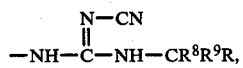

in dilute mineral acid as, for example, dilute aqueous hydrochloric acid.

Finally, many of the compounds of this invention wherein R is $(C_2-C_4)$alkenyl can be readily prepared via a carbodiimide intermediate as illustrated in Flow Chart E.

FLOW CHART E

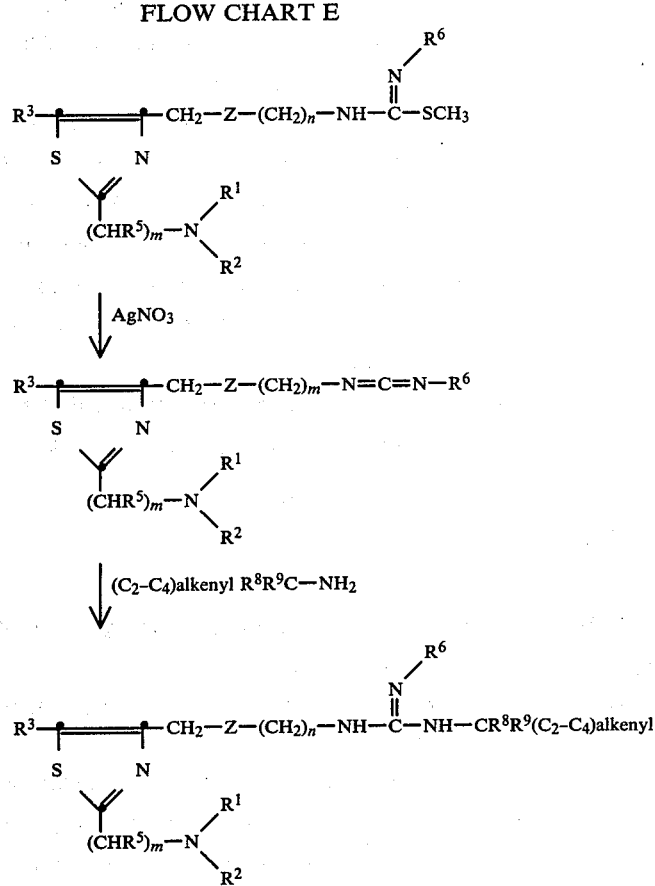

wherein $R^1$, $R^2$, $R^3$, $R^8$, $R^9$, Z, n and m have their previously assigned value and $R^6$ is CN, CO ($C_1$-$C_4$)-alkyl, $CO_2$($C_1$-$C_4$)alkyl, $SO_2$—aryl or $SO_2CH_3$ wherein aryl is phenyl, halophenyl, ($C_1$-$C_4$)alkylphenyl or ($C_1$-$C_4$)-alkyloxyphenyl.

According to Flow Chart E, an isothiourea VIIIa (prepared by the procedure of Flow Chart C or equivalent procedure) is reacted with silver nitrate to prepare a carbodiimide (XIII), reaction of which with a primary amine, $NH_2CR^8R^9$($C_2$-$C_4$)alkenyl, yields those compounds of this invention wherein A is NCN etc. (VI).

In the general case, compounds of formula XX can be prepared by reacting a compound of the formula:

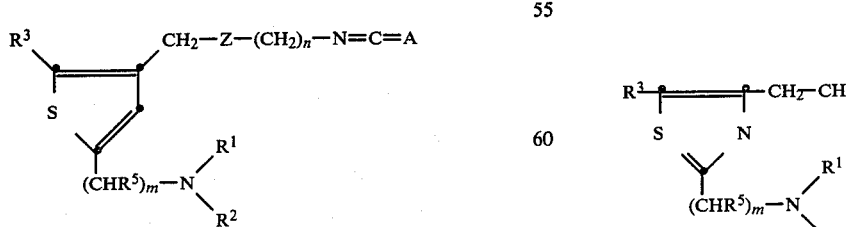

with an amine of formula $NH_2CR^8R^9$($C_2$-$C_4$)alkenyl.

Compounds according to the above formula (XX) wherein Z is $CH_2$ and n is 1, 2 or 3, can be prepared by the procedure illustrated in Flow Chart F below.

FLOW CHART F

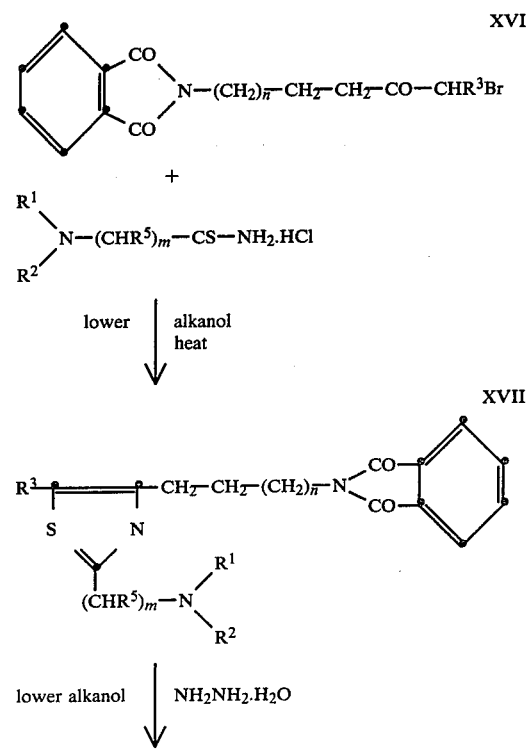

-continued

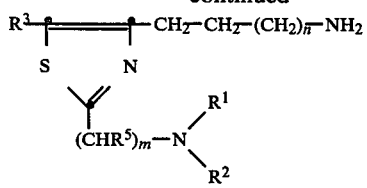

wherein $R^1$, $R^2$, $R^3$, $R^5$, n and m have their previously assigned meaning.

According to flow chart F, an omega (phthalimido)alkyl halomethyl ketone (XVI) is reacted with dimethylaminothioacetamide hydrochloride to produce a 2-aminoalkyl-5-permissibly substituted-4-omega-(phthalimido)alkylthiazole (XVII). The phthalimido group is removed by hydrolysis with hydrazine hydrate to produce the 4-(omega-aminoalkyl)-thiazole ($V_c$). Alkaline hydrolysis with an alkali metal hydroxide followed by treatment with a dilute hydrochloric acid can also be used. This primary amine product (Vc) corresponds to the starting material ($V_a$) produced by flow chart A and can undergo each of the reactions set forth in Flow Charts B-E to produce the compounds of this invention wherein Z in formula XX is $CH_2$.

In the above reaction schemes, the aminoalkyl group present at position 2 of the thiazole ring has been shown as carrying through each of the reaction steps essentially unchanged from the starting material employed (I in Flow Chart A). At times it is desirable to use certain alternate procedures in those instances where either $R^1$ or $R^2$ or both are hydrogen. For example, where $R^1$ is hydrogen but $R^2$ is alkyl, it is possible to use a benzyl protecting group through a given reaction scheme to the preparation of the hydroxymethyl derivative (IV) at which point the benzyl group can be removed by catalytic hydrogenation to give a secondary amine grouping $NHR^2$. Similarly, an acyl protecting group can be used such as a benzoyl group and this protecting group is removed by reduction to an alcohol during the lithium triethylborohydride reduction step by using excess reducing agent. Similarly, if it is desired to have a primary alkylamino group at position 2 of the thiazole ring, a protecting group such as a phthalimido group can be utilized. In such instance, the starting material (I) would be one in which $R^1$ and $R^2$, when taken together with the nitrogen to which they are attached, form a phthalimido group. This grouping can be carried throughout the synthetic procedure until it is desired to remove it (after reaction of the ethylamine to form the side chain) by hydrolysis as with hydrazine. In the preferred synthetic procedure set forth in Flow Chart A, such protecting groups for a secondary aminoalkyl group at position 2 of the thiazole ring is not necessary.

An alternate procedure for preparing intermediate useful in the synthesis of compounds of this invention (XX) starts with the reaction of dichloroacetone and a substituted aminothioacetamide. The use of the resulting 4-chloromethylthiazole where not more than one of $R^1$ and $R^2$ is H has been discussed previously in connection with Flow Chart A. However, this procedure is illustrated in Flow Chart G below and is particularly valuable in preparing the compounds of this invention wherein both $R^1$ and $R^2$ are H.

FLOW CHART G

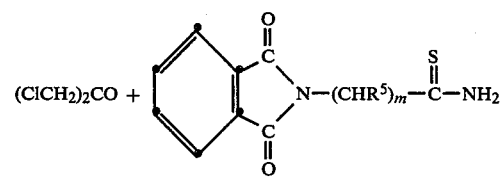

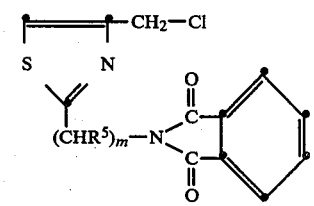

Base 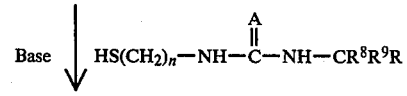

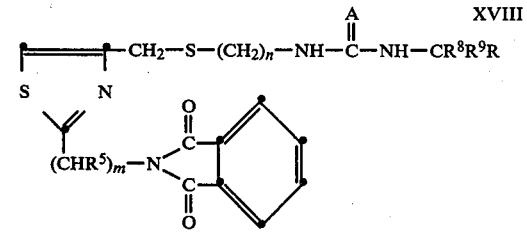

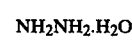

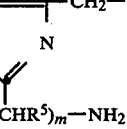
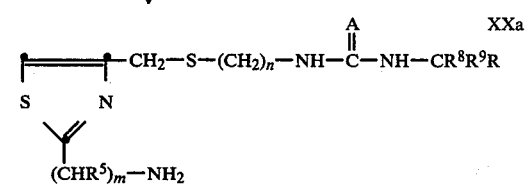

wherein R, $R^5$, $R^8$, $R^9$, A, m and n have their previously assigned significances.

In Flow Chart G, a 2-(phthalimidoalkylthioacetamide) reacts with dichloroacetone, following the procedure of J. Am. Chem. Soc., 64, 90 (1942), to yield a 2-(phthalimidoalkyl)-4-chloromethylthiazole (XVIII). Reaction of this intermediate with a cysteamine (or homocysteamine) derivative in which the amine group is substituted so as to form a desired terminal "amidine" in the presence of base provides a 2-(phthalimido)-4-thiazolyl derivative (XVIII) which can be hydrolyzed with hydrazine to yield the desired 2-aminoalkyl-thiazole derivative (XXa in which $R^1$ and $R^2$ are H, and A and R have their previous scope).

Step 2 of Flow Chart G is a specific example of a general procedure by which a salt of a compound of the formula:

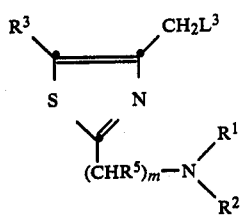

where $L^3$ is a good leaving group, such as halo, preferably chloro; or ester, for example, tosyloxy, brosyloxy or mesyloxy; is reacted in the presence of two equivalents of base with a thiol of formula $$HS(CH_2)_n-NH-CA-NH-CR^8R^9R$$

to give a compound of formula XX.

In Flow Chart G above, a process is illustrated in which a leaving group —chloro— is present on the 4-thiazolemethyl moiety and the thiol group is, for example, a 1-[2-mercaptoethyl (or 3-mercaptopropyl)-amino substituted]-1-alkylamino-2-nitroethenediamine or N-2-mercaptoethyl (or 3-mercaptopropyl)-N'-cyano-N"-alkylguanidine. Alternatively, the leaving group can be present in the ethenediamine or cyanoguanidine moiety and the thiol group present as such or as a pro-SH group in the dialkylaminoalkylthiazole portion, as illustrated below.

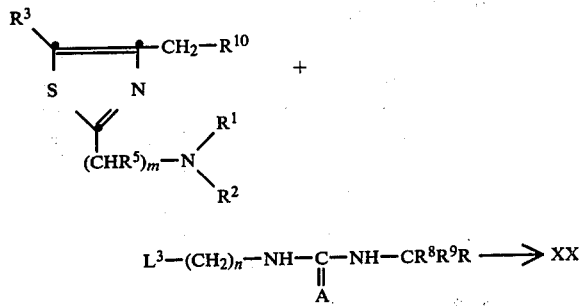

where $R^{10}$ is SH or

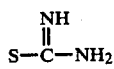

and R, $R^1$, $R^2$, $R^5$, $R^8$, $R^9$, m, n, A and $L^3$ have the same meaning as hereinabove. $L^3$ is preferably Cl or Br, A is preferably CH—$NO_2$ and $R^{10}$ is preferably SH.

One starting material for the above synthesis is prepared by reacting the desired 4-chloromethyl-2-aminoalkylthiazolehydrochloride or other suitable salt (see discussion following Flow Chart A for preparation) with thiourea. The other starting material where A is CH—$NO_2$ is prepared by the method disclosed in Belgian Pat. No. 886,997 and where A is N—CN, in U.S. Pat. No. 4,093,621.

In the above structures, the guanidines and ethenediamine terminal groups have been written with structures K and L since it has been believed that these are the most favored structures

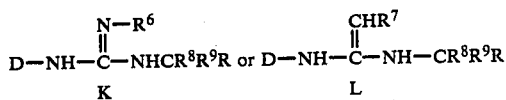

where D is

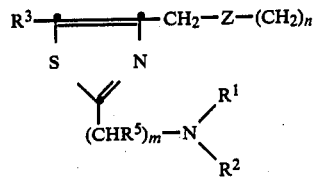

However, as is recognized in the art, K and L represent only one of three possible tautomeric structures, the others being K', K", L' and L".

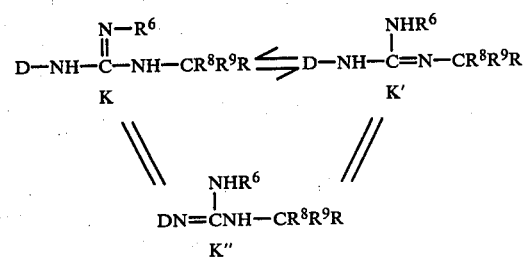

and

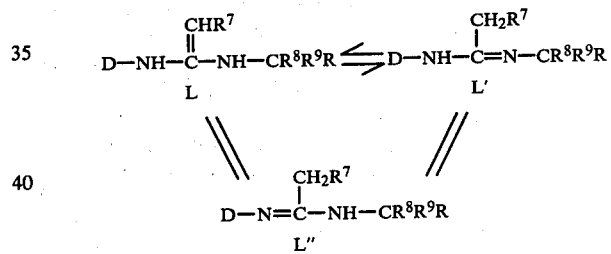

In the above formulas R, $R^1$, $R^2$, $R^3$, $R^5$, $R^6$, $R^8$, $R^9$, Z, m and n have the same meaning previously assigned and $R^7$ is $NO_2$, $SO_2$—$CH_3$ or $SO_2$-aryl. It is understood in the art that such tautomeric forms exist in equilibrium and, depending on the R, $R^6$, $R^7$ etc. substituent, one form may be more favored in a given substitution pattern. It is also understood that portrayal of a given tautomer in a structure is for convenience only and that all tautomeric forms are included in each such written structure.

This invention is further illustrated by the following examples.

EXAMPLE 1

Preparation of Ethyl 2-Dimethylaminomethyl-4-thiazolecarboxylate

A reaction mixture was prepared containing 15.5 g. of dimethylaminothioacetamide hydrochloride, 20.5 g. of ethyl bromopyruvate and 100 ml. of ethanol. The reaction mixture was heated to refluxing temperature for about four hours after which time the solvent was removed in vacuo in a rotary evaporator. The residue, containing ethyl 2-dimethylaminomethyl-4-thiazolecarboxylate hydrochloride formed in the above reaction, was dissolved in a mixture of ether and water. The aqueous layer was separated. The ether layer was extracted with an equal volume of water and then discarded. The two aqueous layers were combined and washed with ether. The ether layer was again discarded and the aqueous layer cooled to a temperature in the range of 0°–5° C. Solid potassium carbonate was added until the aqueous layer gave a basic reaction to litmus. An oil separated comprising ethyl 2-dimethylaminomethyl-4-thiazolecarboxylate free base. The oily layer was extracted with ether and the ether extract separated and dried. The ether was removed by evaporation in vacuo. The resulting residue was purified by gradient high pressure liquid chromatography (silica, ethyl acetate). Ethyl 2-dimethylaminomethyl-4-thiazolecarboxylate thus obtained had the following physical characteristics:

Analysis Calculated: C, 50.45; H, 6.59; N, 13.07; S, 14.96 Found: C, 50.13; H, 6.39; N, 12.89; S, 15.04.

The nmr spectrum in CDCl$_3$ (TMS internal standard) gave the following signals ($\delta$): 1.43 (triplet, 3H), 2.40 (singlet, 6H), 3.87 (singlet, 2H), 4.47 (quartet, 2H), 8.20 (singlet, 1H).

Following the above procedure, a solution containing 20.4 g. of ethyl bromopyruvate and 20.8 g. of N-methyl-N-benzoyl thioacetamide in 100 ml. of ethanol was heated to refluxing temperature for about 4 hours. The solvent was removed by evaporation in vacuo and the resulting residue dissolved in 65 ml. of 4.5N aqueous hydrochloric acid. The aqueous acidic layer was extracted with ether and the ether extract discarded. 11.5 g. of sodium carbonate were added to the aqueous layer. Ethyl 2-(methylbenzoylaminomethyl)-4-thiazolecarboxylate formed in the above reaction, being insoluble in the solution, separated and was extracted into ether. The ether extract was separated and dried. Evaporation of the ether yielded 20.2 g. of ethyl 2-(methylbenzoylaminomethyl)-4-thiazolecarboxylate melting at about 151.5°–153.5° C. after recrystallization from ethyl acetate.

Analysis Calculated: C, 59.19; H, 5.30; N, 9.20; Found: C, 58.98; H, 5.25; N, 8.90.

The nmr spectrum in CDCl$_3$ (TMS internal standard) gave the following signals ($\delta$): 1.42 (triplet, 3H), 3.07 (singlet, 3H), 4.41 (quartet, 2H), 4.98 (singlet, 2H), 7.40 (apparent singlet, 5H), 8.16 (singlet, 1H).

EXAMPLE 2

Preparation of 2-Dimethylaminomethyl-4-thiazolemethanol

A solution of 12.5 g. of ethyl 2-dimethylaminomethyl-4-thiazolecarboxylate dissolved in about 35 ml. of anhydrous tetrahydrofuran was prepared and then cooled to about 0° C. under a nitrogen atmosphere. About 130 ml. of a 1 molar solution of lithium triethylborohydride in THF was added in dropwise fashion while maintaining the temperature in the range 0°–5° C. The reaction mixture was stirred for about two hours after which time 36 ml. of 6N aqueous hydrochloric acid were added while maintaining the temperature in the range −3° C. to 0° C. The volatile constituents were removed in vacuo on a rotary evaporator. Water was added to the resulting residue and again the volatile constituents were removed. Water was again added to the residue and the aqueous mixture extracted several times with ether. The ether extracts were separated and discarded. The aqueous solution was then chilled and made basic by the addition of solid potassium carbonate. The resulting alkaline aqueous mixture was extracted with ethyl acetate. 2-Dimethylaminomethyl-4-thiazolemethanol, being insoluble in the basic solution, separated and was extracted with several portions of ethyl acetate. The ethyl acetate extracts were combined, and the combined extracts washed with saturated aqueous sodium chloride and then dried. The ethyl acetate was removed by evaporation. The residue consisting of a brown oil weighing about 7.7 g. comprised 2-dimethylaminomethyl-4-thiazolemethanol formed in the above reaction having the following physical characteristics.

Analysis Calculated: C, 48.81; H, 7.02; N, 15.26 Found: C, 48.71; H, 6.77; N, 15.85.

The nmr spectrum in CDCl$_3$ (TMS internal standard) gave the following signals ($\delta$): 2.33 (singlet, 6H), 3.74 (singlet, 2H), 4.32 (singlet, 1H), 4.72 (singlet, 2H), 7.15 (singlet, 1H)

Boiling point = 102° C. at 0.5 torr.

Following the above procedure, 22.5 g. of ethyl N-methyl-N-benzoyl 2-aminomethyl-4-thiazolecarboxylate were dissolved in 125 ml. of dry THF under a nitrogen atmosphere. 320 ml. of a 1M LiEt$_3$BH in THF was added. (Excess borohydride was required over the amount in the above example because of the necessity of reducing both the ethyl ester group to a hydroxymethyl group and of removing the benzoyl group as benzyl alcohol leaving a secondary amine). The reaction mixture was worked up in accordance with the above procedure by decomposition with 6N aqueous hydrochloric acid and water. The residue remaining after the volatile constituents had been removed was a thick oil which was taken up in a little water and 60 ml. of ether. 1 ml. of 12N aqueous hydrochloric acid was added, thus making the aqueous phase strongly acidic. The ether layer was separated and the aqueous layer extracted five more times with equal portions of ether. The ether extracts were discarded. The water layer was separated and the water removed by evaporation in vacuo. The acidic residue was made strongly basic (while being cooled) with 50% aqueous hydroxide (6 grams in 6 ml. of water). 2-Methylaminomethyl-4-thiazolemethanol produced by the above series of reactions was insoluble in the alkaline layer and separated. The compound was taken up in ethyl acetate using a continuous extractor. Removal of the solvent left a tannish oily residue weighing 10.7 grams comprising 2-methylaminomethyl-4-thiazolemethanol. The compound was converted to the dihydrochloride salt by standard laboratory procedures.

Alternatively, a mixture of 2.14 g of ethyl 2-dimethylaminomethyl-4-thiazolecarboxylate and 0.38 g of sodium borohydride in 20 ml. of isopropanol was heated with stirring at reflux temperature for about 14 hours. The reaction mixture was cooled, and 2 ml. of water were added carefully followed by 4 ml. of 5N aqueous hydrochloric acid. The volatile constituents were removed by evaporation. Methanol (10 ml.) was added and the mixture heated to refluxing temperature for about one hour. Methanol was removed by evaporation and the residual solids digested in 10 ml. of isopropanol on the stream bath. The isopropanol solution was separated by decantation and the solids reextracted with 10 ml. of isopropanol. The isopropanol solutions and extracts were combined and the combined solution filtered while hot to remove insoluble material. The filtrate was chilled and a crystalline solid appeared which separated and was recovered by filtration. Recrystallization of the filter cake from isopropanol gave 1.73 g of 2-dimethylaminomethyl-4-thiazolemethanol hydrochloride melting at 153°–154° C.

Analysis: calculated: C, 40.28; H, 6.28; Cl, 16.99; N, 13.42 Found: C, 40.38; H, 6.04; Cl, 17.24; N, 13.12.

The methanols produced by the process of this example are readily converted to the corresponding thiazolemethyl chlorides according to the following procedure: A suspension was prepared from 1.05 grams of 2-dimethylaminomethyl-4-thiazolemethanol hydrochloride and 15 ml. of chloroform. Thionyl chloride (2.50 g) was added and the resulting mixture was stirred at reflux temperature for about 2.75 hours. Any volatile constituents including excess thionyl chloride were removed by evaporation. The residue was suspended in chloroform and the chloroform removed by evaporation. The residue was then recrystallized from a methanol-ethyl acetate solvent mixture to yield 2-dimethylaminomethyl-4-thiazolylmethylchloride hydrochloride melting at 136°–8° C.

Analysis: calculated: C, 37.01; H, 5.32; Cl, 31.21; N, 12.33 Found: C, 37.13; H, 5.06; Cl, 31.41; N, 12.36.

EXAMPLE 3

Preparation of 2-(2-Dimethylaminomethyl-4-thiazolylmethylthio)ethylamine

A reaction mixture was prepared from 18.8 g. of 2-dimethylaminomethyl-4-thiazolemethanol, 12.8 g. of 2-aminoethanethiol hydrochloride (cysteamine hydrocloride) and 160 ml. of 48% aqueous hydrobromic acid. The reaction mixture was stirred at about 100° C. for about 11 hours. The volatile constituents were removed in vacuo on a rotary evaporator. Water was added and the volatile constituents again removed by evaporation. The resulting residue, comprising 2-(2-dimethylaminomethyl-4-thiazolylmethylthio)ethylamine trihydrobromide formed in the above reaction, was dissolved in ethanol. The ethanol was evaporated and the resulting residue again dissolved in ethanol. Evaporation of the ethanol yielded a hygroscopic residue which was recrystallized from a methanol-ethyl acetate solvent mixture. 2-(2-Dimethylaminomethyl-4-thiazolylmethylthio)ethylamine trihydrobromide thus prepared had the following physical characteristics:

Analysis calculated: C, 22.80; H, 4.25; Br, 50.56; N, 8.86; S, 13.53 Found: C, 23.02; H, 4.31; Br, 50.64; N, 8.80; S, 13.60

The nmr spectrum in DMSOd6 (TMS internal standard) gave the following signals (δ): 2.55–3.2 (multiplet, 4H), 2.84 (singlet 6H), 3.92 (singlet, 2H), 4.74 (singlet, 2H), 7.2–7.7 (broad, 1H), 7.94 (singlet, 1H), 7.92 (broad, 3H), 10.22 (broad, 1H).

The above primary amine can be prepared by an alternate procedure involving the fusion of a 2-dialkylaminoalkyl-4-thiazolylmethylchloride acid addition salt with an acid addition salt of cysteamine (or homocysteamine). This alternate procedure is illustrated below.

2-Dimethylaminomethyl-4-thiazolylmethylchloride hydrochloride (1.92 g.) and cysteamine hydrochloride (0.96 g.) were intimately mixed and the mixture heated slowly under anhydrous conditions to about 100° C. over a period of one hour. The reaction mixture was then heated in the range 104°–110° C. for a period of 6 hours at which time the reaction was substantially complete as determined by tlc [silica-95:5 ethanol-NH4OH (0.88 sp. gr.)]. The reaction mixture was cooled and the cooled melt dissolved in a minimal amount of water. The solution was transferred to a rotary evaporator and the water removed. The resulting residue solidified and the solid was recrystallized from a methanol-ethyl acetate solvent mixture. Hygroscopic crystals of 2-(2-dimethylaminomethyl-4-thiazolylmethylthio)ethyl amine trihydrochloride thus produced melted at about 165°–72° C. with evolution of HCl.

Analysis calculated: C, 31.72; H, 5.91; Cl, 31.21; N, 12.33; S, 18.82 found: C, 31.63; H, 6.15; Cl, 31.34; N, 12.62; S, 18.63.

Following the above procedure, 10.1 millimoles of 2-(methylaminomethyl)-4-thiazolemethanol dihydrochloride, 1.15 g. of cysteamine hydrochloride and 15 ml. of 48% aqueous hydrobromic acid were stirred at about 100° C. for about 7.5 hours. Water and hydrobromic acid were removed on a rotary evaporator and the resulting residue comprising 2-(2-methylaminomethyl-4-thiazolylmethylthio)ethylamine trihydrobromide formed in the above reaction was dissolved in water and the water removed by evaporation. The residue was again taken up in water and the water removed by evaporation. The residue was then dissolved in a small volume of water and a solution of 5.5 g. of potassium carbonate in 15 ml. of water was added. The resulting alkaline solution was evaporated to dryness. The resulting residue, comprising the free base of 2-(2-methylaminomethyl-4-thiazolylmethylthio)ethylamine, was slurried with ethanol and the ethanol separated and removed by evaporation. The residue was twice slurried with isopropanol. The residue was next extracted with boiling isopropanol several times and the combined isopropanol extracts combined and filtered. Removal of the isopropanol yielded a yellow oil. The yellow oil was dissolved in chloroform and the coloroform solution filtered. Chloroform was evaporated from the filtrate to yield 1.59 g. of a yellow oil comprising 2-(2-methylaminomethyl-4-thiazolylmethylthio)ethylamine. The compound had the following physical characteristics:

The nmr spectrum in CDCl3 (TMS internal standard) gave the following signals (δ): 1.53 (overlapping singlets, 3H), 2.53 (singlet 3H), 2.62 (triplet, 2H), 2.86 (triplet, 2H), 3.81 (singlet, 2H), 4.04 (singlet, 2H), 7.04 (singlet, 1H).

EXAMPLE 4

Preparation of N-2-propynyl-N'-2-(2-dimethylaminomethyl-4-thiazolylmethylthio)ethyl-N"-cyanoguanidine A solution was prepared from 3.07 g. of dimethyl cyanodithioimidocarbonate and 35 ml. of ethanol. A second solution containing 4.62 g. of 2-(2-dimethylaminomethyl-4-thiazolylmethylthio)ethylamine in 50 ml. of ethanol was added in dropwise fashion with stirring to the first solution over a period of about 1.5 hours. The resulting reaction mixture was stirred for an additional 20 hours after which time the volatile constituents were removed in a rotary evaporator. Chromatography of the residue over silica by gradient elution using ethyl acetate containing increasing quantities of methanol as the eluant yielded fractions containing methyl N-2-(2-dimethylaminomethyl-4-thiazolylmethylthio)ethyl-N'-cyanocarbamidothioate, formed in the above reaction. These fractions were combined and the solvent removed from the combined fractions in a rotary evaporator. The residue weighed 4.8 g. and, after recrystallization from carbon tetrachloride, melted at about 75°–77° C.

Analysis Calculated: C, 43.74; H, 5.81; N, 21.25; S, 29.19 Found: C, 43.46; H, 5.71; N, 20.98 S, 29.15 1.32 Grams of the above thioester and 1.98 g of redistilled propargylamine dissolved in 6 ml. of anhydrous methanol, and the solution stirred at reflux temperature under a positive nitrogen pressure for 5 hours, an additional gram of propargylamine was added and the reaction mixture refluxed for an additional 6 hours. The solvent and excess amine were then removed by evaporation on a rotary evaporator. The residue was purified by gradient elution high pressure liquid chromatography (silica-ethyl acetate-methanol). Fractions containing N-2-propynyl-N'-2-(2-dimethylaminomethyl-4-thiazolylmethylthio)ethyl-N''-cyanoguanidine formed in the above reaction as shown by TLC were combined to yield 0.96 g. of a glassy residue upon evaporation of the solvent.

$R_f = 0.33$ (silica, 5:95 NH$_4$OH; ethanol).

Mass spectrum; m/e 337.

The nmr spectrum in CDCl$_3$ (TMS internal standard) shows the following signals ($\delta$): 2.33 (singlet, 6H); 2.28 (multiplet, 1H); 2.73 (triplet, 2H); 3.43 (doublet of triplets, 2H); 3.72 (singlet, 2H); 3.80 (singlet, 2H); 4.0 (multiplet, 2H); 6.36 (multiplet, 1H); 6.63 (multiplet, 1H); 7.01 (singlet, 1H).

Following the above procedure, but substituting allylamine for propargylamine in the reaction with N-2-(2-dimethylaminomethyl-4-thiazolylmethylthio)ethyl-N'-cyanocarbamidothioate, N-allyl-N'-2-(2-dimethylaminomethyl-4-thiazolylmethylthio)ethyl-N''-cyanoguanidine was prepared. Yield=0.28 g from 600 mg of thioester.

Analysis calculated for C$_{13}$H$_{22}$N$_6$S$_2$: C, 51.82; H, 6.83; N, 21.58; Found: C, 51.81; H, 6.57; N, 21.28

The nmr spectrum in CDCl$_3$ (TMS internal standard) shows the following peaks ($\delta$): 2.36 (singlet, 6H); 2.73 (triplet, 2H); 3.45 (doublet of triplets, 2H); 3.75 (singlet, 2H); 3.82 (singlet, 2H); 3.95 (multiplet, 2H); 5.32 (multiplet, 2H); 5.92 (triplet, 1H); 6.11 (triplet, 1H); 5.61–6.1 (multiplet, 1H); 7.10 (singlet, 1H).

EXAMPLE 5

Preparation of N-(2-propynyl)-N'-2-(2-dimethylaminomethyl-4-thiazolylmethylthio)ethyl 2-nitro-1,1-ethanediamine.

A quantity of 2-(2-dimethylaminomethyl-4-thiazolylmethylthio)ethylamine trihydrobromide prepared from 50 g. of 2-dimethylaminomethyl-4-thiazolylmethanol by the procedure of Example 3 were dissolved in 150 ml. of water. A solution of 125 g. of potassium carbonate and 150 ml. of water was carefully added thereto. The water was removed by evaporation in vacuo. The resulting alkaline residue was triturated with ethanol and isopropanol and the alkanols removed therefrom by evaporation. The resulting residue was extracted several times with hot isopropanol and the isopropanol extracts were filtered to remove inorganic salts. Evaporation of the solvent from the filtrate yielded a residue which was dissolved in chloroform and filtered. The chloroform was removed from the filtrate on a rotary evaporator. The resulting residue comprised the free base of 2-(2-dimethylaminomethyl-4-thiazolylmethylthio)ethylamine. 1.16 g. of the free base were dissolved in 8 ml. of water at 48° C. This solution was added to a stirred suspension of 0.82 g. of 1-(2-propynyl)amino-1-methylthio-2-nitroethyleneamine (prepared according to the procedure of U.S. Pat. No. 4,203,909). The mixture was stirred at 48° C. for about 2.75 hours after the addition had been completed. The aqueous reaction mixture was extracted with ethyl acetate. The ethyl acetate was evaporated from the extract and the residue subjected to high pressure liquid chromatography (silica, 1% ethanolic NH$_4$OH). Appropriate fractions as determined by TLC were combined and the solvent removed by evaporation. The resulting residue was recrystallized from ethyl acetate to yield N-2-propynyl-N'-2-(2-dimethylaminomethyl-4-thiazolylmethylthioethyl 2-nitro-1,1-ethenediamine melting at about 90°–92° C.

Analysis Calculated: C, 47.30; H, 5.95; N, 15.70 O, 9.00 Found: C, 47.57; H, 5.69; N, 15.77 O, 9.27

EXAMPLE 6

Preparation of N-(2-propynyl)-N'-2-[2-(4-morpholinomethyl)-4-thiazolylmethylthio]ethyl 2-nitro-1,1-ethenediamine Following the procedure of Example 1, 4-morpholinothioacetamide hydrochloride was condensed with ethyl bromopyruvate to yield ethyl 2-(4-morpholinomethyl)-4-thiazolecarboxylate, melting at 129°–130° C. after recrystallization from a methylene dichloride-ethyl acetate solvent mixture.

Analysis Calculated: C, 51.54; H, 6.29; N, 10.93. Found: C, 51.36; H, 6.05; N, 10.88.

Following the procedure of Example 2, the above ester was reduced to the corresponding thiazolemethanol, 2-(4-morpholinomethyl)-4-thiazolemethanol, having an nmr spectrum in CDCl$_3$ (TMS internal standard) showing the following signals ($\delta$): 2.55 (multiplet, 4H); 3.35–3.90 (singlet plus multiplet, 6H), 4.70 (3H), 7.13 (singlet, 1H).

Reaction of the thiazolemethanol with cysteamine hydrochloride by the procedure of Example 3 yielded 2-[2-(4-morpholinomethyl)-4-thiazolylmethylthio]ethylamine having the following physical characteristics:

nmr spectrum in CDCl$_3$ (TMS internal standard) showing the following signals ($\delta$): 1.83 (singlet, 2H), 2.3–3.1 (multiplet, 8H), 3.4–3.9 (multiplet plus singlets, 8H), 7.03 (singlet, 1H).

Following the procedure of Example 5, the 2-[2-(4-morpholinomethyl)-4-thiazolylmethylthio]ethylamine can be reacted with N-(2-propynyl)-1-methylthio-2-nitroethyleneamine to yield N-(2-propynyl)-N'-2-[2-(4-morpholinomethyl)-4-thiazolylmethylthio]ethyl-2-nitro-1,1-ethenediamine.

EXAMPLE 7

Preparation of N-allyl-N'-2-[2-(1-pyrrolidinomethyl)-4-thiazolylmethylthio]ethyl 2-nitro-1,1-ethenediamine The same sequence of reactions as in Example 6 were carried out starting with 1-pyrrolidinomethylthioacetamide hydrochloride to yield the following intermediates.

Ethyl 2-(1-pyrrolidino)-4-thiazolecarboxylate. M.P.=81°–81.5° C. after recrystallization from a toluene-ethyl acetate solvent mixture.

nmr spectrum in CDCl$_3$ (TMS internal standard) showed the following signals ($\delta$): 1.40 (triplet 3H), 1.82 (multiplet, 4H), 2.70 (multiplet, 4H), 4.02 (singlet, 2H), 4.45 (quartet, 2H), 8.17 (singlet, 1H).

2-(1-pyrrolidinomethyl)-4-thiazolemethanol. nmr spectrum in CDCl$_3$ (TMS internal standard) gave the following signals ($\delta$): 1.77 (multiplet, 4H), 2.65 (multiplet, 4H), 3.92 (singlet, 2H), 4.73 (singlet, 3H), 7.15 (singlet, 1H).

2-[2-(1-pyrrolidinomethyl)-4-thiazolyl]-methylthio]ethylamine trihydrobromide was crystallized from isopropanol.

The ethylamine obtained from the above hydrobromide can be reacted with N-allyl-1-methylthio-2-nitroethyleneamine to yield N-allyl-N'-2-[2-(1-pyrrolidinomethyl)-4-thiazolylmethylthio]ethyl 2-nitro-1,1-ethenediamine.

EXAMPLE 8

Preparation of N-(2-propynyl)-N'-2-[2-(1-piperidinomethyl)-4-thiazolylmethylthio]ethyl 2-nitro-1,1-ethenethiamine Following the sequence of reactions of Example 6, the following intermediates were produced from 1-piperidinothioacetamide hydrochloride.

Ethyl 2-(1-piperidinomethyl)-4-thiazolecarboxylate melting at 95°–97° C.

nmr in CDCl$_3$ (TMS internal standard) gave the following signals ($\delta$): 1.40 (triplet, 3H), 1.53 (multiplet, 6H), 2.53 (multiplet, 4H), 3.85 (singlet, 2H), 4.45 (quartet, 2H), 8.20 (singlet, 1H).

2-(1-piperidinomethyl)-4-thiazolemethanol having an nmr spectrum in CDCl$_3$ (TMS internal standard) which gave the following signals ($\delta$): 1.53 (multiplet, 6H), 2.47 (multiplet, 4H), 3.77 (singlet, 2H), 4.77 (singlet, >3H), 7.13 (singlet, 1H).

2-[2-(1-piperidinomethyl)-4-thiazolylmethylthio]ethylamine trihydrobromide crystallized from isopropanol. The nmr spectrum in DMSOd$_6$ (TMS internal standard) showed the following signals ($\delta$): 1.77 (multiplet, 6H), 2.6–3.8 (8H, multiplets), 3.97 (singlet, 2H), 4.80 (singlet, 2H), 7.80 (singlet, 1H), 8.12 (broad, 3H).

The primary amine obtained from the above salt can be reacted by the procedure of Example 6 with N-(2-propynyl)-1-methylthio-2-nitroethyleneamine to yield N-(2-propynyl)-N'-2-[2-(1-piperidinomethyl)-4-thiazolylmethylthio]ethyl 2-nitro-1,1-ethenediamine.

EXAMPLE 9

Preparation of N-(2-propynyl)-N'-2-[2-(methylethylaminomethyl)-4-thiazolylmethylthio]ethyl 2-nitro-1,1-ethenediamine.

Following the reaction sequence of Example 6 starting with the reaction of N-methyl-N-ethyl aminothioacetamide hydrochloride and ethyl bromopyruvate, the following intermediates were prepared:

Ethyl 2-(methylethylaminomethyl)-4-thiazolecarboxylate, a non-crystallizable oil 2-(methylethylaminomethyl)-4-thiazolemethanol having an nmr spectrum in CDCl$_3$ (TMS internal standard) showing the following signals ($\delta$): 1.10 (triplet, 3H), 2.33 (singlet, 3H), 2.53 (quartet, 2H), 3.80 (singlet, 2H), 4.73 (singlet, 2H), 5.30 (singlet, 1H), 7.20 (singlet, 1H).

2-[2-(methylethylaminomethyl)-4-thiazolylmethylthio]ethylamine having an nmr spectrum in CDCl$_3$ (TMS internal standard) showing the following signals ($\delta$): 1.08 (triplet, 3H), 1.57 (singlet, 2H), 2.33 (singlet, 3H), 2.2–3.0 (multiplets, 6H), 3.78 (apparent singlet, 4H), 7.03 (singlet, 1H).

The above primary amine can be reacted with N-(2-propynyl)-1-methylthio-2-nitroethyleneamine to yield N-(2-propynyl)-N'-2-[2-(methylethylaminomethyl)-4-thiazolylmethylthio]ethyl 2-nitro-1,1-ethenediamine.

EXAMPLE 10

Preparation of N-3-(2-dimethylaminomethyl-4-thiazolylmethylthio)propyl-N'-allyl 2-nitro-1,1-ethenediamine.

Following the procedure of Example 3, 10 g of 2-dimethylaminomethyl-4-thiazolylmethanol, 9.2 g of homocysteamine (3-aminopropanethiol) hydrobromide and 100 ml of 48% aqueous hydrobromic acid were heated to reflux temperature for about six hours. Volatile constituents were removed by evaporation and the crystalline residue was triturated with isopropanol. The isopropanol was decanted. This procedure was repeated several times. The crystalline product was finally filtered to yield 7.0 g of 3-(2-dimethylaminomethyl-4-thiazolylmethylthio)propylamine trihydrobromide melting at 179°–181° C. (hydroscopic).

Analysis: calculated: C, 24.61; H, 4.54; Br, 49.11; N, 8.61; found: C, 24.46; H, 4.34; Br, 49.31; N, 8.38

Following the procedure of Example 5, the above thiazolylmethylthiopropylamine can be reacted with 1-allylamino-1-methylthio-2-nitroethylene to yield N-3-(2-dimethylaminomethyl-4-thiazolylmethylthio)-propyl-N'-allyl 2-nitro-1,1-ethenediamine.

EXAMPLE 11

Preparation of N-2-(2-dimethylaminomethyl-4-thiazolylmethylthio)ethyl-N'-propynyl-N''-methylsulfonylguanidine A solution containing 755 mg. of dimethyl methanesulfonylimidodithiocarbonate and 975 mg. of 2-(2-dimethylaminomethyl-4-thiazolylmethylthio)ethylamine in 14 ml. of ethanol was stirred at ambient temperature for about 18 hours. The volatile components were removed by evaporation in vacuo, leaving a glassy residue comprising methyl N-2-(2-dimethylaminomethyl-4-thiazolylmethylthio)ethyl-N'-methanesulfonylcarbamidothioate having the following physical characteristics:

Mass spectrum: m/e 383 (p+1)

R$_f$ 0.62 (silica, 5:95, NH$_4$OH: ethanol)

The glassy residue was dissolved in 6 ml. of methanol. Two g. of propargylamine were added and the solution stirred at refluxing temperature under a positive nitrogen blanket for about 5 hours. An additional gram of propargylamine was added and the solution refluxed for an additional 2 hours. The solvent and excess amine were removed by evaporation. The resulting residue comprising N-2-(2-dimethylaminomethyl-4-thiazolylmethylthio)ethyl-N'-propynyl-N''-methylsulfonylguanidine was purified by HPLC using a gradient elution technique (ethyl acetate, ethanol). Fractions containing the desired product were combined and the solvent removed therefrom in vacuo. Two hundred mg. of N-2-(2-dimethylaminomethyl-4-thiazolylmethylthio)ethyl-N'-propynyl-N''-methylsulfonylguanidine were obtained as a glass with the following physical characteristics:

Mass spectrum: m/e 390 (p+1)

The nmr spectrum in CDCl$_3$ (TMS) shows the following peaks: ($\delta$): 2.33 (singlet, 6H); 2.35 (multiplet, 1H); 2.70 (triplet, 2H); 2.90 (singlet, 2H); 2.95 (singlet, 1H); 3.40 (doublet of triplets, 2H); 3.70 (singlet 2H); 3.78 (singlet, 2H); 3.98 (multiplet, 2H); 6–7 (broad, 2H); 7.05 (singlet, 1H).

EXAMPLE 12

Preparation of N-methallyl-N'-2-(3-dimethylamino)propyl-4-thiazolylmethylthio]ethyl-2-nitro-1,1-ethenediamine A reaction mixture was prepared containing 95.2 g. of 4-dimethylaminobutyronitrile, 134.3 g. of pyridine, 257.6 g. of triethylamine and 113 g. of H$_2$S. The reaction mixture was placed in an autoclave and the autoclave shaken for about 16 hours at 55° C. The reaction mixture was then removed from the autoclave and the volatile constituents removed by evaporation in vacuo. The resulting residue comprising 4-dimethylaminothiobutyramide formed in the above reaction was digested with about 1.5 l. of boiling ethyl acetate. The mixture thus produced was filtered through cellulose (hyflo supercel). The filtrate was concentrated until crystals appeared. The crystals were separated by filtration and the separated crystals washed with ethyl acetate. Sixty grams of 4-dimethylaminothiobutyramide melting at about 77° C. were obtained.

Analysis: calculated: C, 49.27; H, 9.65; N, 19.15
found: C, 49.07; H, 9.59; N, 18.99.

A suspension was prepared from 14.6 g. of 4-dimethylaminothiobutyramide in 50 ml. of ethanol. The suspension was chilled. A cold solution of 3.65 g. of anhydrous hydrogen chloride in 50 ml. of anhydrous ethanol was added followed by 21.5 g. of ethyl bromopyruvate. The resulting reaction mixture was stirred at ambient temperature for about one hour and then was heated to refluxing temperature for an additional 2.25 hours. The volatile constituents were removed by evaporation in vacuo and the resulting residue taken up in a mixture of water and diethyl ether. The aqueous layer was separated and the separated layer extracted with several equal portions of ether. The aqueous solution was again chilled and then made basic (pH=10) by the addition of solid sodium bicarbonate and sodium carbonate. Ethyl 2-(3-dimethylamino)propyl-4-thiazolecarboxylate, being insoluble in the alkaline aqueous solution, separated and was extracted into ether. The ether extracts were combined and dried and the ether removed therefrom by evaporation in vacuo yielding 21 g. of the ester as an oil. The compound had the following physical characteristics:

Thin layer chromatography (silica-95:5 ethanol/ammonia solvent system): $R_f$=0.43.

nmr (CDCl$_3$-TMS)δ: 1.46 (triplet, 3H); 2.27 (singlet, 6H); 1.8–2.6 (multiplets, approx. 4H); 3.24 (triplet, 2H); 4.43 (quartet, 2H); 8.04 (singlet, 1H).

Following the procedure of Example 2, ethyl 2-(3-dimethylamino)propyl-4-thiazolecarboxylate was reduced with lithium triethylborohydride to yield 2-(3-dimethylamino)propyl-4-thiazolemethanol as an oil. The compound had the following physical characteristics.

Thin layer chromatography, $R_f$=0.42 (silica-95:5 ethanol/ammonium hydroxide solvent system).

nmr (CDCl$_3$-TMS)δ: 2.15 (singlet, 6H); 1.62–2.50 (multiplets, approx. 4H); 2.05 (triplet, 2H); 3.75 (very broad, approx. 1H); 4.65 (singlet, 2H); 7.0 (singlet, 1H).

About 2.0 g. of the above 4-thiazolemethanol were dissolved in ethanol to which was added 0.36 g. of anhydrous hydrogen chloride in ethanol. The ethanol was removed by evaporation and the resulting residue triturated with ethyl acetate. Crystallization occurred and the crystals were separated by filtration. Recrystallization from a mixture of methanol and ethyl acetate gave 2-(3-dimethylamino)propyl-4-thiazolemethanol hydrochloride melting at 125°–127° C.

Analysis: calculated: C, 45.66; H, 7.24; N, 11.83
found: C, 45.38; H, 7.39; N, 11.63.

A reaction mixture was prepared from 1.43 g. of the above thiazolemethanol hydrochloride, an equal weight of thionyl chloride and 35 ml. of chloroform. The reaction mixture was heated to refluxing temperature with stirring for about 3.5 hours. The volatile constituents were removed in vacuo and the crystalline residue was triturated with ethyl acetate. The ethyl acetate suspension was filtered. Recrystallization of the filter cake from a mixture of methanol and ethyl acetate yielded 4-(chloromethyl)-N,N-dimethyl-2-thiazolepropanamine hydrochloride melting at 149°–151° C.

Analysis: calculated: C, 42.36; H, 6.32; Cl, 27.78
found: C, 42.11; H, 6.18; Cl, 27.57.

A reaction mixture was prepared from 1.35 g. of 4-(chloromethyl)-N,N-dimethyl-2-thiazolepropanamine hydrochloride and 0.60 g. of 2-aminoethanethiol hydrochloride. The reaction mixture was heated at about 105° C. and agitated with a magnetic stirrer for one hour. The reaction mixture which melted was kept at about 105° C. for an additional 6.5 hours. Upon cooling, an amorphous solid formed which was dissolved in water and 0.8 g. of potassium carbonate in water added. The water was removed by evaporation. The resulting residue was triturated with ethanol and the ethanol removed by evaporation. The trituration-evaporation process was repeated twice with isopropanol. The residue was then extracted five times with 8 ml. portions of boiling isopropanol. The combined isopropanol extracts were filtered and the isopropanol removed by evaporation in vacuo. About 1.4 g. of 2-[2-(3-dimethylamino)-propyl-4-thiazolylmethylthio]ethylamine were obtained as a glass. The compound had the following physical characteristics.

Thin layer chromatography: $R_f$=0.21 (silica-95:5 ethanol/ammonium hydroxide).

nmr (CDCl$_3$-TMS) δ: 2.00 (quintet, 2H); 2.40 (singlet, 6H); 1.75–3.40 (overlapping multiplets, more than 10H); 3.80 (singlet, 2H); 5.75 (broad, 2.6H; 6.90 (singlet, 1H).

Following the procedure of Example 5, 2-[2-(3-dimethylamino)propyl-4-thiazolylmethylthio]ethylamine can be reacted with N-methallyl-1-methylthiol-2-nitroethyleneamine to yield N-methallyl-N'-2-[2-(3-dimethylamino)propyl-4-thiazolylmethylthio]ethyl 2-nitro-1,1-ethenediamine.

EXAMPLE 13

Preparation of N-allyl-N'-2-[2-(2-dimethylamino)ethyl-4-thiazolylmethylthio]ethyl 2-nitro-1,1-ethenediamine A reaction mixture was prepared from 22.4 g. of N,N-dimethylcyanoacetamide, 21 ml. of liquid hydrogen sulfide and 1 ml. of triethylamine. The reaction mixture was placed in an autoclave and the autoclave shaken at about 55° C. for about 12 hours. The reaction mixture was taken from the autoclave and the volatile constituents removed by evaporation. Ethanol was added to the residue, thus producing a crystalline solid. The solid was filtered and the filter cake washed with cold ethanol. Twenty-one grams of 3-amino-3-thioxo-N,N-dimethylpropanamide were obtained melting at 111°–114° C. The compound had the following nmr (CDCl$_3$+DMSOd$_6$)δ: 3.07 (doublet, 6H); 3.82 (singlet, 2H); 9.1 (very broad, 1H).

A reaction mixture was prepared from 21 g. of 3-amino-3-thioxo-N,N-dimethylpropanamide, 21 ml. of ethyl bromopyruvate and 200 ml. of ethanol. The reaction mixture was heated to refluxing temperature for 1.5 hours after which time the ethanol was removed by evaporation. A crystalline solid remained which was triturated with ethanol and again filtered. Recrystallization of the crude product from ethanol yielded 20.5 g. of ethyl 2-dimethylaminocarbonylmethylene-4- thiazolecarboxylate hydrobromide melting at about 150°–153° C. The compound had the following nmr (CDCl$_3$)δ: 1.43 (triplet, 3H); 3.10 (doublet, 6H); 4.45 (quartet, 2H); 5.02 (singlet, 2H); 8.33 (singlet, 1H); 10.6 (singlet, 1H).

A solution was prepared from 20.5 g. of ethyl 2-dimethylaminocarbonylmethylene-4-thiazolecarboxylate, hydrobromide, 50 ml. of ethanol and 50 ml. of water. One hundred twenty-seven ml. of 1N aqueous sodium hydroxide were added and the resulting solution stirred for about 24 hours at room temperature. The ethanol was then removed by evaporation. The aqueous layer was extracted with ether and the ether discarded. Sixty-three and one half ml. of 1N aqueous hydrochloric acid were then added. The acidic aqueous solution was chilled overnight and a crystalline solid which precipitated comprising 2-dimethylaminocarbonylmethylene-4-thiazolecarboxylic acid was separated by filtration. The filter cake was washed with a small amount of cold water. 7.85 g. of product were obtained melting at 187°–188° C. An additional 4.40 g. of 2-dimethylaminomethylcarbonylmethylene-4-thiazolecarboxylic acid were obtained from the mother liquor.

Analysis: calculated: C, 44.87; H, 4.70; N, 13.08 found: C, 44.60; H, 4.76; N, 12.87.

A suspension of 4.28 g. of 2-dimethylaminocarbonylmethylene-4-thiazolecarboxylic acid in 50 ml. of THF was kept at about 15° C. under a nitrogen atmosphere. 80 ml. of a 1M borane solution in THF were added. The reaction mixture was stirred for three hours at about 10° C. after which time it was cooled to 0° C. and 10 ml. of methanol were added in dropwise fashion. The reaction mixture was then allowed to remain overnight at room temperature. The volatile constituents were removed by evaporation in vacuo. Twenty ml. of methanol and 10 ml. of 6N aqueous hydrochloric acid were added to the residue. The resulting solution was heated to refluxing temperature on a steam bath for 1.5 hours. The methanol was then removed by evaporation and 4.5 g. of sodium bicarbonate were added to the remaining aqueous solution. Water was removed from this solution in vacuo and the solid residue triturated with ethanol. The ethanol was removed by evaporation. This trituration process was repeated twice using isopropanol. The residual solid was then extracted four times with boiling isopropanol. The isopropanol extracts were filtered and the isopropanol removed from the filtrate by evaporation. 4.1 g. of an oil comprising 2-(2-dimethylamino)ethyl-4-thiazolemethanol were obtained. The compound was purified using high-pressure liquid chromatography over silica with ethanol as the eluant. 0.9 g. of product were obtained having the following nmr (CDCl$_3$+DMSOd$_6$)δ: 1.42 (singlet, 6H); 2.7–3.4 (overlapping triplets, 4H); 4.65 (singlet, 2H); 4.8 (broad, greater than 1H); 7.00 (singlet, 1H).

Following the procedure of Example 2, 2-(2-dimethylamino)ethyl-4-thiazolemethanol was converted to 2-(2-dimethylamino)ethyl-4-thiazolemethylchloride hydrochloride with thionyl chloride. Then following the procedure of Example 3, the chloride hydrochloride was reacted with cysteamine hydrochloride to yield 2-[2-(2-dimethylamino)ethyl-4-thiazolylmethylthio]-ethylamine. This compound can be in turn converted by the method of Example 6 to N-allyl-N′-2-[2-(2-dimethylamino)ethyl-4-thiazolylmethylthio]ethyl 2-nitro-1,1-ethenediamine.

EXAMPLE 14

Preparation of 1-allyl-1-[2-(2-dimethylaminomethyl-4-thiazolylmethylthio)]ethyl 2-nitro-1,1-ethenediamine A reaction mixture was prepared containing 696 mg. of 1-[2-(2-dimethylaminomethyl-4-thiazolylmethylthio)ethyl]amino-1-methylthio-2-nitroethylene, 230 mg. of allylamine and 3 ml. of ethanol. The reaction mixture was stirred at room temperature for about 17 hours. The volatile constituents were removed by evaporation. The resulting residue was crystallized from ethanol and the ethanol removed by evaporation. The crystalline residue was then recrystallized from ethyl acetate to yield 630 mg. of 1-allyl-1-[2-(2-dimethylaminomethyl-4-thiazolylmethylthio)]ethyl 2-nitro-1,1-ethenediamine melting at 94.5°–96.5° C. A second recrystallization from ethyl acetate yielded 530 mg. of 1-allyl-1-[2-(2-dimethylaminomethyl-4-thiazolylmethylthio)]ethyl 2-nitro-1,1-ethenediamine melting at 95.5°–97.5° C.

Analysis Calculated: C, 47.04; H, 6.49; N, 19.59; O, 8.95 Found: C, 46.87; H, 6.47; N, 19.30; O, 9.11

In flow chart A above, compound I is a substituted aminothioacetamide hydrohalide of the structure

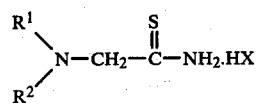

Where the substituting groups are alkyl, the compounds are known as, for example, dimethylaminothioacetamide, diethylaminothioacetamide, etc. and can be prepared by the method of *J. Org. Chem.*, (Russia), 6, 884 (1970) in English.

Illustrated preparations are given below.

Preparation 1

Morpholinothioacetamide

A reaction mixture was prepared from 203 ml. each of triethylamine and pyridine plus 63 g. of morpholinoacetonitrile. Hydrogen sulfide was bubbled through the heated, stirred reaction mixture for about 2.5 hours. Stirring was continued overnight at ambient temperature. The next day, H$_2$S was passed through the heated, stirred reaction mixture for an additional 1.5 hours. At this point, the solvents were evaporated in vacuo and the residue triturated with ether. The ether was discarded and the residue dissolved in ethanol. Crystalline morpholinothioacetamide precipitated and was separated by filtration. Treatment of the filtrate with alcoholic hydrogen chloride yielded morpholinothioacetamide hydrochloride melting in the range 64°–80° C. See also *J.A.C.S.*, 72, 2804 (1950).

Following the above procedure but using piperidinoacetonitrile in place of morpholinoacetonitrile, there was prepared piperidinothioacetamide hydrochloride melting at 166°–168° C., after recrystallization from ethylacetate. See also *Helv. Chim. Act.*, 43, 659 (1960).

Yield 35 g. from 62 g. of piperidinoacetonitrile starting material.

Following the above procedure using 100 g. of pyrrolidinoacetonitrile, there were obtained 68.4 g. of pyrrolidinothioacetamide hydrochloride (new) melting at about 195°–197° C.

Analysis calculated: C, 39.88; H, 7.25; N, 15.50 S, 17.74 Found: C, 39.66; H, 6.99; N, 15.76; S, 17.84

Following the above procedure but using 49 g. of methylethylaminoacetonitrile, 200 ml. of triethylamine and 200 ml. of benzene, there was prepared N-methyl-N-ethylaminothioacetamide hydrochloride (new) melting at 115°–117° C.

The compounds of formula XX are potent $H_2$-receptor antagonists and thus anti-ulcer agents. The relation of the $H_2$-receptors to mammalian gastric secrection is described in an article by Black et al. *Nature*, 236, 385 (1972).

The following assay for $H_2$-receptor blocking activity was employed. Female albino rats were treated with estrone 24 hours prior to the initiation of the experiment. The rats were sacrificed and the uterine horns removed therefrom and suspended at ambient temperatures in isolated organ baths containing De Jalon's solution. After equilibration, the uterine strips are exposed to 50 millimole aqueous potassium chloride, which produces a sustained contraction. When the uterus is so contracted, histamine produces a dose-dependent $H_2$-receptor-mediated relaxation. A control dose-response curve to histamine is constructed on each tissue. Following thorough washout of the histamine after obtaining the control dose-response curve, each antagonist (the compounds of this invention) is added for 30 minutes at a concentration of $10^{-5}$ molar. The uterine strips are then contracted with aqueous potassium chloride in the presence of the antagonist and a second dose-response curve to histamine obtained. In the presence of a competitive antagonist, the dose-response curve to histamine is shifted in parallel to the right with no depression of the maximum relative to the control curve. The dose ratio (DR) is calculated for each concentration of antagonist by dividing the $ED_{50}$ of histamine in the presence of the competitive antagonist by the control $ED_{50}$ for histamine. The dissociation constant ($K_B$) of the antagonist is calculated from the dose-ratios by the following equation:

$$K_B = [\text{antagonist}]/(DR-1)$$

Cimetidine is included as an internal standard.

Results of the above assay carried out on N-(2-propynyl)-N'-2-(2-dimethylaminomethyl-4-thiazolyl-methylthio)ethyl 2-nitro-1,1-ethenediamine indicated that the compound had a $pA_2(-\log K_B) = 6.73$, which is approximately 3.63 times higher affinity for the $H_2$-receptors than cimetidine. Another compound of this invention, N-(2-propynyl)-N'-2-(2-dimethylaminomethyl-4-thiazolylmethylthio)ethyl-N''-cyanoguanidine has a $pA_2$ value of 6.0.

A second assay for $H_2$-receptor blocking activity employs the isolated bullfrog gastric mucosa—see Warrick and Lin, *Communications in Chem. Pathology and Pharmacology*, 13, 149 (1976). The assay is carried out as follows: The gastric mucosa of the bullfrog (*Rana catesbeiana*) is separated from the musculature of the stomach and placed between a pair of Ussing chambers made of lucite. The chambers are filled with frog Ringer solution and acid secretion is stimulated by addition of histamine to the serosal side of the mucosa at a final concentration of $10^{-5}$ M/l. Acid output is automatically titrated to pH 4.5. After steady response to $10^{-5}$ M/l of histamine is established, the antagonist (a compound of this invention) is added to the serosal chamber and the maximal inhibition by each concentration of the $H_2$-antagonist is recorded. From the dose-response curve, the $ED_{50}$ of the drug is calculated. The relative potency of each unknown antagonist is calculated by dividing the $ED_{50}$ for cimetidine by the $ED_{50}$ of the drug in question. N-(2-propynyl)-N'-2-(2-dimethylaminomethyl-4-thiazolylmethylthio)ethyl 2-nitro-1,1-ethenediamine had a relative potency of 6.17 compared to 1.0 for cimetidine.

An in vivo assay for antisecretory action of drugs on acid secretion utilizes gastric fistula dogs with vagally innervated gastric fistula and vagally denervated Heidenhain pouch. In this procedure, a steady-state gastric secretion is produced by the iv infusion of histamine. The antisecretory drugs under test are given either intravenously by infusion over a 30 minute period or orally 75 min. prior to collection of gastric secretion from the fistula. The $ED_{50}$ (iv) for N-(2-propynyl)-N'-2-(2-dimethylaminomethyl-4-thiazolylmethylthio)ethyl 2-nitro-1,1-ethenediamine is 0.068μ moles/kg/30 min., over 7 times smaller than that found for cimetidine.

In utilizing the compounds of this invention an antisecretory agents, either the parenteral or oral route of administration may be employed.

In one embodiment of the invention, there is provided a pharmaceutical formulation which comprises as an active ingredient, a compound of formula XX, or a pharmaceutically-acceptable salt thereof, associated with one or more pharmaceutically-acceptable carriers therefor. Orally-acceptable formulations such as capsules or tablets constitute the preferred mode of administration.

For oral dosage, a suitable quantity of a free base of this invention, or a pharmaceutically-acceptable salt thereof, is mixed with one or more conventional excipients such as starch and the mixture placed in telescoping gelatin capsules or compressed into tablets each typically containing from 100–400 mg. of active ingredients. The tablets may be scored if lower or divided dosages are to be used. For parenteral administration via an iv infusion, an isotonic solution of a salt is preferably employed although a soluble free base is also useful in isotonic preparations.

Oral administration of about 100–150 mg. of three to four times a day will suffice to control acid secretion in ulcer patients and thus alleviate ulcer symptoms. Generally, however, the compounds of this invention are administered to humans orally in a daily dosage range of 300–800 mg. Smaller dosages at more frequent intervals may also be employed. The preferred oral dosage range is about 5–10 mg./kg./day of mammalian body weight, although a dosage range of from 5–20 mg./kg./day can be used.

I claim:

1. N-(2-propynyl)-N'-2-(2-dimethylaminomethyl-4-thiazolylmethylthio)ethyl 2-nitro-1,1-ethenediamine.

2. A pharmaceutical formulation in unit dosage form adapted for oral administration to achieve an antisecretory effect, comprising per dosage unit an antisecretorially-effective amount of a compound of claim 1 plus one or more pharmaceutical excipients.

3. A method for inhibiting gastric acid secretion in mammals which comprises administering to a mammal whose gastric acid secretion is excessive and who is in need of treatment an antisecretorially-effective amount of a compound according to claim 1.

* * * * *